(12) United States Patent
Hanson et al.

(10) Patent No.: US 9,370,650 B2
(45) Date of Patent: Jun. 21, 2016

(54) METHOD AND ARTICLES FOR TREATING THE SINUS SYSTEM

(71) Applicant: ENTELLUS MEDICAL, INC., Plymouth, MN (US)

(72) Inventors: Anthony J. Hanson, Chaska, MN (US); John R. Drontle, Monticello, MN (US); Chad Harris, Albertville, MN (US); Matthew Higgins, Maple Grove, MN (US)

(73) Assignee: ENTELLUS MEDICAL, INC., Plymouth, MN (US)

( * ) Notice: Subject to any disclaimer, the term of this patent is extended or adjusted under 35 U.S.C. 154(b) by 0 days.

(21) Appl. No.: 14/468,617

(22) Filed: Aug. 26, 2014

(65) Prior Publication Data

US 2014/0364700 A1 Dec. 11, 2014

Related U.S. Application Data

(63) Continuation of application No. 13/277,885, filed on Oct. 20, 2011, now Pat. No. 8,834,513, which is a continuation-in-part of application No. 12/479,521, filed on Jun. 5, 2009, now Pat. No. 8,282,667.

(60) Provisional application No. 61/405,035, filed on Oct. 20, 2010.

(51) Int. Cl.
  *A61B 17/42* (2006.01)
  *A61M 29/02* (2006.01)
  (Continued)

(52) U.S. Cl.
  CPC ............... *A61M 29/02* (2013.01); *A61B 1/06* (2013.01); *A61B 17/24* (2013.01);
  (Continued)

(58) Field of Classification Search
  CPC ..... A61F 5/08; A61B 17/24; A61B 2017/246
  USPC .......... 606/191–199; 604/532, 96.01, 101.04, 604/97.01–100.03, 103.09; 600/199, 101, 600/178, 182; 362/572
  See application file for complete search history.

(56) References Cited

U.S. PATENT DOCUMENTS 2,525,183 A 10/1950 Robison
3,800,788 A 4/1974 White
(Continued)

FOREIGN PATENT DOCUMENTS

EP 0 129 634 1/1985
EP 1598015 11/2005
(Continued)

OTHER PUBLICATIONS

Petersen, Robert J., Canine Fossa Puncture, The Laryngoscope Office, Oct. 5, 1972, pp. 369-371.
(Continued)

*Primary Examiner* — Tuan V Nguyen
*Assistant Examiner* — Kevin Everage
(74) *Attorney, Agent, or Firm* — Vista IP Law Group LLP

(57) ABSTRACT

A method of treating a sinus cavity of a subject includes advancing a distal portion of a light source through a drainage pathway of a sinus cavity and into the sinus cavity and visually observing a transdermal light emitted from the light source. A distal portion of a substantially rigid inner guide member of a balloon dilation catheter is advanced into the drainage pathway, the balloon dilation catheter including a movable shaft including a balloon that is slidably mounted on the substantially rigid inner guide member. The movable shaft and balloon are advanced distally over the substantially rigid inner guide member to place a portion of the balloon in the drainage pathway whereby the balloon is inflated.

13 Claims, 14 Drawing Sheets

(51) Int. Cl.
   *A61B 17/24*     (2006.01)
   *A61B 1/06*      (2006.01)
   *A61F 5/08*      (2006.01)
   *A61B 19/00*     (2006.01)
   *A61B 17/00*     (2006.01)

(52) U.S. Cl.
   CPC .............. *A61B 19/5202* (2013.01); *A61F 5/08* (2013.01); *A61B 19/5244* (2013.01); *A61B 2017/00734* (2013.01); *A61B 2019/521* (2013.01); *A61B 2019/5206* (2013.01); *A61M 2029/025* (2013.01); *A61M 2210/0681* (2013.01)

(56) References Cited

U.S. PATENT DOCUMENTS

| | | | |
|---|---|---|---|
| 4,737,141 | A | 4/1988 | Spits |
| 5,021,043 | A | 6/1991 | Becker et al. |
| 5,024,658 | A | 6/1991 | Kozlov et al. |
| 5,169,386 | A | 12/1992 | Becker et al. |
| 5,391,199 | A | 2/1995 | Ben-Haim |
| 5,415,634 | A | 5/1995 | Glynn et al. |
| 5,443,489 | A | 8/1995 | Ben-Haim |
| 5,466,222 | A | 11/1995 | Ressemann et al. |
| 5,470,315 | A | 11/1995 | Adams |
| 5,588,950 | A | 12/1996 | Sano et al. |
| 5,632,762 | A | 5/1997 | Myler |
| 5,645,528 | A | 7/1997 | Thome |
| 5,795,325 | A | 8/1998 | Valley et al. |
| 5,964,767 | A | 10/1999 | Tapia et al. |
| 6,083,188 | A | 7/2000 | Becker |
| 6,090,132 | A | 7/2000 | Fox |
| 6,113,567 | A | 9/2000 | Becker |
| 6,206,870 | B1 | 3/2001 | Kanner |
| 6,238,364 | B1 | 5/2001 | Becker |
| 6,491,940 | B1 | 12/2002 | Levin |
| 6,543,452 | B1 | 4/2003 | Lavigne |
| D501,677 | S | 2/2005 | Becker |
| 6,851,424 | B2 | 2/2005 | Scopton |
| 7,500,971 | B2 | 3/2009 | Chang et al. |
| 7,520,876 | B2 | 4/2009 | Ressemann et al. |
| 7,678,099 | B2 | 3/2010 | Ressemann et al. |
| 7,785,315 | B1 | 8/2010 | Muni et al. |
| 7,842,062 | B2 | 11/2010 | Keith et al. |
| 7,879,061 | B2 | 2/2011 | Keith et al. |
| 7,918,871 | B2 | 4/2011 | Truitt et al. |
| 8,146,400 | B2 | 4/2012 | Goldfarb et al. |
| 8,241,266 | B2 | 8/2012 | Keith et al. |
| 8,277,478 | B2 | 10/2012 | Drontle et al. |
| 8,282,667 | B2 | 10/2012 | Drontle et al. |
| 8,348,969 | B2 | 1/2013 | Keith et al. |
| 8,568,439 | B2 | 10/2013 | Keith et al. |
| 8,585,728 | B2 | 11/2013 | Keith et al. |
| 8,585,729 | B2 | 11/2013 | Keith et al. |
| 8,623,043 | B1 | 1/2014 | Keith et al. |
| 8,657,846 | B2 | 2/2014 | Keith et al. |
| 8,801,670 | B2 | 8/2014 | Drontle et al. |
| 8,888,686 | B2 | 11/2014 | Drontle et al. |
| 8,915,938 | B2 | 12/2014 | Keith et al. |
| 8,986,340 | B2 | 3/2015 | Drontle et al. |
| 9,005,284 | B2 | 4/2015 | Ressemann |
| 2002/0065455 | A1 | 5/2002 | Ben-Haim |
| 2002/0138121 | A1 | 9/2002 | Fox |
| 2004/0064083 | A1 | 4/2004 | Becker |
| 2004/0064150 | A1 | 4/2004 | Becker |
| 2004/0068299 | A1 | 4/2004 | Laske et al. |
| 2005/0059931 | A1 | 3/2005 | Garrison et al. |
| 2005/0240147 | A1 | 10/2005 | Makower |
| 2005/0245906 | A1 | 11/2005 | Makower |
| 2005/0251119 | A1 | 11/2005 | Eaton et al. |
| 2006/0004286 | A1 | 1/2006 | Chang |
| 2006/0004323 | A1 | 1/2006 | Chang |
| 2006/0063973 | A1 | 3/2006 | Makower |
| 2006/0095066 | A1 | 5/2006 | Chang |
| 2006/0100687 | A1 | 5/2006 | Fahey |
| 2006/0106361 | A1 | 5/2006 | Muni |
| 2006/0149310 | A1 | 7/2006 | Becker |
| 2006/0210605 | A1 | 9/2006 | Chang |
| 2006/0284428 | A1 | 12/2006 | Beadle et al. |
| 2006/0293612 | A1 | 12/2006 | Jenson et al. |
| 2007/0005094 | A1 | 1/2007 | Eaton |
| 2007/0073269 | A1* | 3/2007 | Becker ................. A61M 3/0295 604/509 |
| 2007/0129751 | A1 | 6/2007 | Muni et al. |
| 2007/0135789 | A1 | 6/2007 | Chang et al. |
| 2007/0135803 | A1 | 6/2007 | Belson |
| 2007/0167682 | A1 | 7/2007 | Goldfarb et al. |
| 2007/0208252 | A1 | 9/2007 | Makower |
| 2007/0208301 | A1 | 9/2007 | Evard et al. |
| 2007/0249896 | A1 | 10/2007 | Goldfarb |
| 2007/0250105 | A1 | 10/2007 | Ressemann et al. |
| 2007/0270644 | A1 | 11/2007 | Goldfarb et al. |
| 2007/0282305 | A1 | 12/2007 | Goldfarb et al. |
| 2007/0293726 | A1 | 12/2007 | Goldfarb et al. |
| 2007/0293727 | A1 | 12/2007 | Goldfarb et al. |
| 2008/0015472 | A1 | 1/2008 | Ressemann et al. |
| 2008/0015540 | A1 | 1/2008 | Muni et al. |
| 2008/0033353 | A1* | 2/2008 | Truitt et al. ................. 604/96.01 |
| 2008/0082045 | A1 | 4/2008 | Goldfarb et al. |
| 2008/0097154 | A1* | 4/2008 | Makower ........... A61B 1/00135 600/114 |
| 2008/0097239 | A1 | 4/2008 | Chang et al. |
| 2008/0097295 | A1 | 4/2008 | Makower et al. |
| 2008/0097400 | A1 | 4/2008 | Chang et al. |
| 2008/0097514 | A1 | 4/2008 | Chang et al. |
| 2008/0097515 | A1 | 4/2008 | Chang et al. |
| 2008/0097516 | A1 | 4/2008 | Chang et al. |
| 2008/0103521 | A1 | 5/2008 | Makower et al. |
| 2008/0119693 | A1 | 5/2008 | Makower et al. |
| 2008/0125626 | A1 | 5/2008 | Chang |
| 2008/0132938 | A1 | 6/2008 | Chang et al. |
| 2008/0154237 | A1 | 6/2008 | Chang et al. |
| 2008/0154250 | A1 | 6/2008 | Makower et al. |
| 2008/0172033 | A1 | 7/2008 | Keith |
| 2008/0195041 | A1 | 8/2008 | Goldfarb et al. |
| 2008/0228085 | A1 | 9/2008 | Jenkins et al. |
| 2008/0234720 | A1 | 9/2008 | Chang et al. |
| 2008/0269596 | A1 | 10/2008 | Revie et al. |
| 2008/0275483 | A1* | 11/2008 | Makower et al. ............. 606/192 |
| 2008/0281156 | A1 | 11/2008 | Makower et al. |
| 2008/0287908 | A1 | 11/2008 | Muni et al. |
| 2008/0319424 | A1 | 12/2008 | Muni et al. |
| 2009/0005763 | A1 | 1/2009 | Makower et al. |
| 2009/0028923 | A1 | 1/2009 | Muni et al. |
| 2009/0030274 | A1 | 1/2009 | Goldfarb et al. |
| 2009/0073718 | A1 | 3/2009 | Chung |
| 2009/0093823 | A1 | 4/2009 | Chang et al. |
| 2009/0132033 | A1* | 5/2009 | Maurer et al. ................. 623/2.11 |
| 2009/0187098 | A1 | 7/2009 | Makower et al. |
| 2009/0198216 | A1 | 8/2009 | Muni et al. |
| 2009/0204142 | A1* | 8/2009 | Becker ................. A61M 1/0084 606/192 |
| 2009/0216196 | A1 | 8/2009 | Drontle |
| 2010/0030113 | A1 | 2/2010 | Morriss et al. |
| 2010/0168511 | A1 | 7/2010 | Muni et al. |
| 2010/0211007 | A1 | 8/2010 | Lesch |
| 2010/0241155 | A1 | 9/2010 | Chang et al. |
| 2010/0274222 | A1 | 10/2010 | Setliff, III et al. |
| 2011/0071349 | A1 | 3/2011 | Drontle et al. |
| 2011/0224652 | A1 | 9/2011 | Drontle et al. |
| 2012/0010646 | A1 | 1/2012 | Keith et al. |
| 2012/0283625 | A1 | 11/2012 | Keith et al. |
| 2013/0030458 | A1 | 1/2013 | Drontle et al. |
| 2013/0030459 | A1 | 1/2013 | Drontle et al. |
| 2013/0041463 | A1 | 2/2013 | Ressemann |
| 2013/0072958 | A1 | 3/2013 | Ressemann et al. |
| 2013/0123833 | A1 | 5/2013 | Lesch et al. |
| 2014/0350520 | A1 | 11/2014 | Drontle et al. |
| 2014/0357959 | A1 | 12/2014 | Hanson |
| 2014/0378776 | A1 | 12/2014 | Hanson |
| 2015/0031950 | A1 | 1/2015 | Drontle et al. |

(56) References Cited

U.S. PATENT DOCUMENTS

| | | |
|---|---|---|
| 2015/0045827 A1 | 2/2015 | Drontle et al. |
| 2015/0105818 A1 | 4/2015 | Keith et al. |
| 2016/0038726 A1 | 2/2016 | Hanson et al. |

FOREIGN PATENT DOCUMENTS

| | | |
|---|---|---|
| WO | WO 91/17787 | 11/1991 |
| WO | WO 96/00033 | 1/1996 |
| WO | WO 2005/086945 | 9/2005 |

OTHER PUBLICATIONS

Elidan, J., MD., Irrigation of the Maxillary Sinus by Canine Fossa Puncture Experience with 202 Patients, Ann Otol Rhinol Laryngol, 92:1983, pp. 528-529.

Yanagisawa, Eiji, et al., Trans-Canine-Fossa Maxillary Sinoscopy for Biopsy Via the Stammberger Technique, ENT Rhinoscopic Clinic, Aug. 2001 Rhino, pp. 1-3.

Yanagisawa, Eiji, et al., Powered Endoscopic Inferior Meatal Antrostomy Under Canine Fossa Telescopic Guidance, ENT-Ear, Nose & Throat Journal, Sep. 2001, pp. 618-620.

Sathananthar, Shanmugam, et al., Canine Fossa Puncture and Clearance of the Maxillary Sinus for the Severely Diseased Maxillary Sinus, The Laryngoscope 115: Jun. 2005, pp. 1026-1029.

Robinson, Simon, et al., Patterns of Innervation of the Anterior Maxilla: A Cadaver Study with Relevance to Canine Fossa Puncture of the Maxillary Sinus, Laryngoscope 115: Oct. 2005, pp. 1785-1788.

Bolger, William, E., et al., Catheter-Based Dilation of the Sinus Ostia: Initial Safety and Feasibility Analysis in a Cadaver Model, Maryland Sinus Clinic, Bethesda, Maryland, and California Sinus Institute, Palo Alto, California, OceanSide Publications, Inc., May-Jun. 2006, vol. 20, No. 3, pp. 290-294.

Friedman, Michael, M.D. et al., Functional Endoscopic Dilatation of the Sinuses (FEDS): Patient Selection and Surgical Technique, Operative Technologies in Otolaryngology, vol. 17, No. 2, Jun. 2006, pp. 126-134.

Jones, Nick, Commentary on "Safety and Feasibility of Balloon Catheter Dilation of Paranasal Sinus Ostia: A Preliminary Investigation", Annals of Otology, Rhinology & Laryngology 115(4), pp. 300-301 (2006).

Bolger, William E., Commentary Misconceptions Regarding Balloon Catheter Dilation of Paranasal Sinus Ostia, Annals of Otology, Rhinology & Laryngology 115(10): 791-792 (2006).

Lanza, Donald, C., et al., Commentary Balloon Sinuplasty: Not Ready for Prime Time, Annals of Otology, Rhinology & Laryngology 115(10): 789-790 (2006).

Brown, Christopher, L., et al., "Safety and Feasibility of Balloon Catheter Dilation of Paranasal Sinus Ostia: A Preliminary Investigation", Annals of Otology, Rhinology & Laryngology 115(4):293-299 (2006).

Gottman, D., et al., "Balloon Dilatation of Recurrent Ostia Occlusion of the Frontal Sinus", ECR Mar. 3, 2001, 2:-3:30 PM, Vienna Austria (1 page).

Entellus Medical, 510(k) Premarket Notification cover letter and Attachment B: Predicate Device Labeling, dated Aug. 15, 2007.

R. Peterson, Sinus Puncture Therreapy: Canine Fossa Puncture Method "How I Do It" Head and Neck, The Larynsgoscope 91: Dec. 1981, pp. 2126-2128.

T.G.A. Ijaduola, Use of a Foley Catheter for Short-Tem Drainage of Frontal Sinus Surgery, Journ. of Laryngology and Otology, Apr. 1989, vol. 103, pp. 375-378.

A. Gatot et al., Early Treatment of Oribital Floor Fractures with Catheter Balloon in Childre, Int'l J. of Ped. Otorhinolaryngology, 21 (1991) 97-101.

D.I. Tarasov et al., Treatment of Chronic Ethmoiditis by IntraCellular Administration of Medicines to the Ethmoidal Labyrinth, Vestn Otorinolaringol. Nov.-Dec. 1978; (6):45-47 (Abstract in English).

J.M. Robison, Pressure Treatment of Maxillary Sinusitis, J.A.M.A., May 31, 1952, pp. 436-440.

J M. Robison, Pressure Treatment of Purulent Maxillary Sinusitis, Texas State Journal of Medicine, May 1952, pp. 281-288.

Entellus Medical, 510(k) Letter (Amendment 1) and Attachment D&E, dated Mar. 13, 2008.

Gottman et al., Balloon Dilation of Recurrent Ostial Occlusion of the Frontal Sinus, Gottman et al.: Abstract (B-0453) Mar. 2001, 22 pages.

PCT International Search Report for PCT/US2007/088834, Applicant: Entellus Medical, Inc., Forms PCT/ISA/220 and PCT/ISA/210, dated May 20, 2008 (4 pages).

PCT Written Opinion for PCT/US2007/088834, Applicant: Entellus Medical, Inc., Forms PCT/ISA/237, dated May 20, 2008 (10 pages).

PCT International Search Report for PCT/US2007/66187, Applicant: Entellus Medical, Inc., Forms PCT/ISA/220 and PCT/ISA/210, dated Apr. 17, 2008 (5 pages).

PCT Written Opinion for PCT/US2007/66187, Applicant: Entellus Medical, Inc., Forms PCT/ISA/237, dated Apr. 17, 2008 (5 pages).

Folweiler, David S., Nasal Specific Technique as Part of a Chropractic Approach to Chronic Sinusitis and Sinus Headaches, Journal of Manipulative and Physiological Therapeutics, vol. 18, No. 1 (Jan. 1995).

PCT International Preliminary Report on Patentability (Chapter I of the Patent Cooperation Treaty) of the International Bureau for PCT/US2007/066187, Applicant: Entellus Medical, Inc., Form PCT/IB/326, dated Oct. 30, 2006 (4 pages).

Medtronic, ENT Image-Guided Surgery System, http://www.xomed.com/xomed_products_element.html, Jun. 3, 2009 (2 pages).

PCT International Preliminary Report on Patentability (Chapter I of the Patent Cooperation Treaty) for PCT/US2010/037508, Applicant: Entellus Medical Inc., Form PCT/IB/326 and 373, dated Dec. 15, 2011 (6pages).

Fiber-optic Surgical Probe, http://www.anthonyproducts.com/store/p-389-fiber-optic-surgical-probe.aspx, 1 page, at least as early as Jul. 12, 2011.

Light Probe Kit, http://www.fiberoptix.com/products/light-probe-kit.html, 2 pages, Apr. 2010.

International Search Report dated Aug. 2, 2010, for PCT/US2010/037508, Applicant: Entellus Medical, Inc. (4 pages).

Written Opinion of the International Search Authority dated Aug. 2, 2010, for PCT/US2010/037508, Applicant: Entellus Medical, Inc. (4 pages).

Iro, H., J. Zenk. "A new device for frontal sinus endoscopy: First Clinical Report", Department of Otorhinolaryngology, University of Eralngen-Nuremberg, Germany. Otorhinolaryngology, Head and Neck Surgery vol. 125 No. 6, Dec. 2001, pp. 613-616 (4 pages).

International Preliminary Report on Patentability dated Jul. 30, 2009, for PCT/US2007/088834, Applicant: Entellus Medical, Inc. (9 pages).

File History of U.S. Appl. No. 14/460,912, filed: Aug. 15, 2014, inventor: Anthony J. Hanson, including Office Action dated Feb. 10, 2015 (26pages).

File History of U.S. Appl. No. 14/468,595, filed: Aug. 26, 2014, inventor: Anthony J. Hanson, including Office Action dated Jan. 28, 2015 (26pages).

Final Office Action dated Sep. 22, 2015 in U.S. Appl. No. 14/468,595, filed Aug. 26, 2014, (16pp).

Final Office Action dated Oct. 5, 2015 in U.S. Appl. No. 14/460,912, filed Aug. 15, 2014, (15pp).

Office Action dated Feb. 18, 2016 in U.S. Appl. No. 14/468,595, filed Aug. 26, 2014, (9pp).

\* cited by examiner

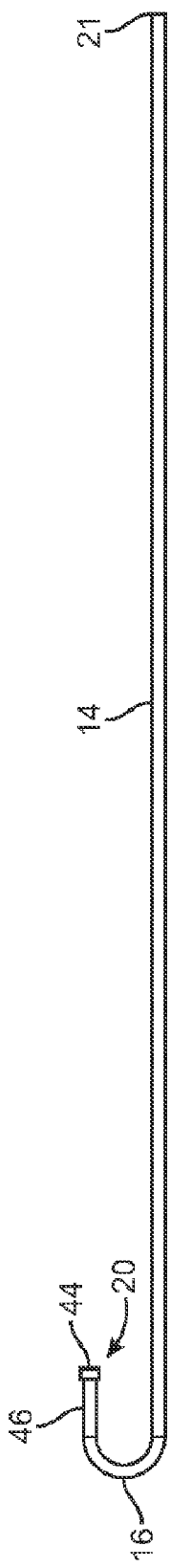
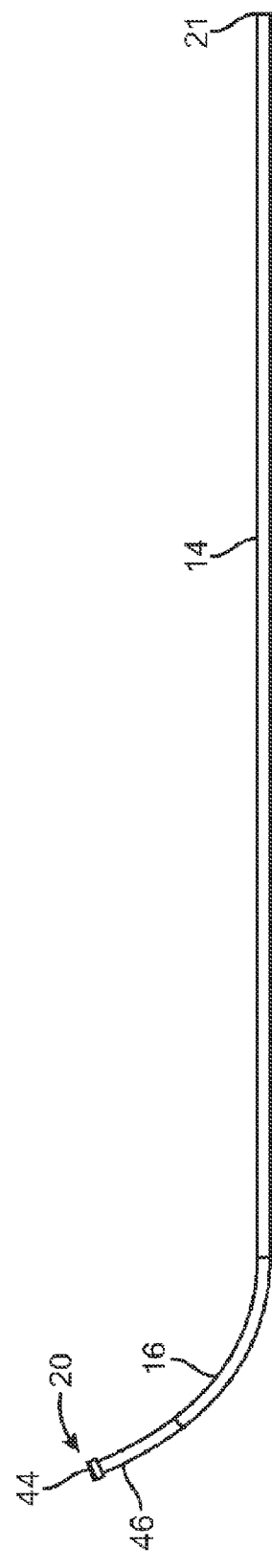
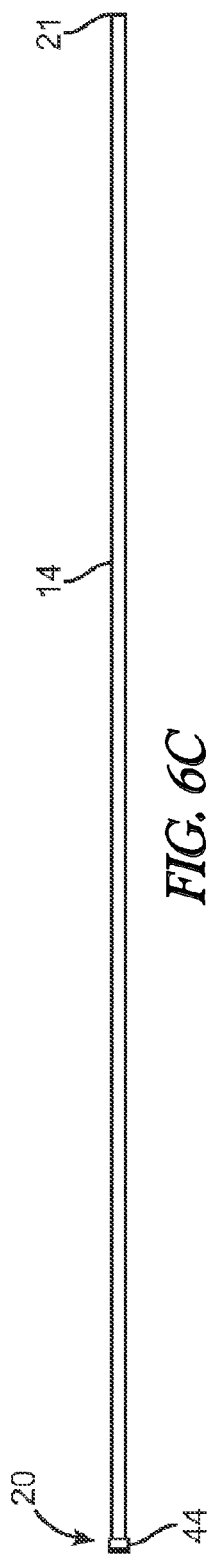
FIG. 6A
FIG. 6B
FIG. 6C

METHOD AND ARTICLES FOR TREATING THE SINUS SYSTEM

RELATED APPLICATIONS

This Application is a continuation of U.S. application Ser. No. 13/277,885 filed on Oct. 20, 2011, now issued as U.S. Pat. No. 8,834,513, which itself is a continuation-in-part of U.S. application Ser. No. 12/479,521 filed on Jun. 5, 2009, now issued as U.S. Pat. No. 8,282,667. The '885 Application also claims priority to U.S. Provisional Patent Application No. 61/405,035 filed on Oct. 20, 2010. Priority is claimed pursuant to 35 U.S.C. §§119 and 120. The above-noted Patent Applications are incorporated by reference as if set forth fully herein.

FIELD OF THE INVENTION

The field of the invention relates to balloon dilation devices, devices for illuminating nasal and sinus cavities, and methods for the treatment of sinusitis.

BACKGROUND OF THE INVENTION

Sinusitis is a condition affecting over 35 million Americans, and similarly large populations in the rest of the developed world. Sinusitis occurs when one or more of the four paired sinus cavities (i.e., maxillary, ethmoid, frontal, sphenoid) becomes obstructed, or otherwise has compromised drainage. Normally the sinus cavities, each of which are lined by mucosa, produce mucous which is then moved by beating cilia from the sinus cavity out to the nasal cavity and down the throat. The combined sinuses produce approximately one liter of mucous daily, so the effective transport of this mucous is important to sinus health.

Each sinus cavity has a drainage pathway or outflow tract opening into the nasal passage. This drainage passageway can include an ostium, as well as a "transition space" in the region of the ostia, such as the "frontal recess," in the case of the frontal sinus, or an "ethmoidal infundibulum," in the case of the maxillary sinus. When the mucosa of one or more of the ostia or regions near the ostia become inflamed, the egress of mucous is interrupted, setting the stage for an infection and/or inflammation of the sinus cavity, i.e., sinusitis. Though many instances of sinusitis may be treatable with appropriate medicates, in some cases sinusitis persists for months or more, a condition called chronic sinusitis, and may not respond to medical therapy. Some patients are also prone to multiple episodes of sinusitis in a given period of time, a condition called recurrent sinusitis.

Balloon dilation has been applied to treat constricted sinus passageways for the treatment of sinusitis. These balloon dilation devices typically involve the use of an inflatable balloon located at the distal end of a catheter such as a balloon catheter. Generally, the inflatable balloon is inserted into the constricted sinus passageway in a deflated state. The balloon is then expanded to open or reduce the degree of constriction in the sinus passageway being treated to facilitate better sinus drainage and ventilation.

Exemplary devices and methods particularly suited for the dilation of anatomic structures associated with the maxillary and anterior ethmoid sinuses are disclosed, for example, in U.S. Pat. No. 7,520,876 and U.S. Patent Application Publication No. 2008-0172033. Other systems have been described for the treatment of various other sinuses including the frontal sinus. For example, U.S. Patent Application Publication No. 2008-0097295 discloses a frontal sinus guide catheter (FIG. 6B) and method of treating the frontal sinuses (e.g., FIGS. 8B-8C). U.S. Patent Application Publication No. 2008-0125626 discloses another guide device (e.g., FIGS. 10C and 10C') for transnasal access to the frontal sinuses for treatment.

SUMMARY OF THE INVENTION

In a first embodiment of the invention, a balloon dilation catheter includes a substantially rigid inner guide member and a movable shaft coupled to a balloon that is slidably mounted on the substantially rigid inner guide member. To treat a drainage pathway of a sinus cavity (e.g., frontal sinus cavity) of a subject using the balloon dilation catheter, the substantially rigid inner guide member is advanced into a drainage pathway of the subject via a nasal passageway. The shaft and balloon are then advanced in a distal direction over the substantially rigid inner guide member to place the balloon in the drainage pathway. This enables the balloon to track over the inner guide member. The balloon is inflated to expand or otherwise remodel the drainage pathway. Where the sinus cavity is the frontal sinus cavity the drainage pathway is the frontal recess.

In another aspect of the invention, a device for dilating the outflow tract of a sinus cavity includes a substantially rigid inner guide member having a proximal end and a distal end and a shaft coupled to a balloon, the shaft having a first lumen along at least a portion thereof containing the substantially rigid inner guide member, the shaft having a second lumen operatively coupled to the interior of the balloon. A handle is disposed along a proximal portion of the substantially rigid inner guide member, the handle including a moveable knob operatively coupled to the shaft, wherein distal advancement of the knob advances the shaft and balloon over the substantially rigid inner guide in a distal direction.

In further aspects of the invention, taught herein are methods of treating a sinus cavity of a subject. In some embodiments the method includes advancing a distal portion of a light source through a drainage pathway of a frontal sinus cavity of a subject and into the frontal sinus cavity; visually observing a transdermal light emitted from the distal portion of the light source in the frontal sinus cavity; advancing a distal portion of a substantially rigid inner guide member of a balloon dilation catheter into the drainage pathway of the frontal sinus cavity, the balloon dilation catheter including a movable shaft slidably mounted on the substantially rigid inner guide member, the movable shaft including a balloon; advancing the movable shaft and balloon distally over the substantially rigid inner guide member to place a portion of the balloon in the drainage pathway; and inflating the balloon.

BRIEF DESCRIPTION OF THE DRAWINGS

FIG. 6A is a side view of an inner guide member according to one embodiment.

FIG. 6B is a side view of an inner guide member according to another embodiment.

FIG. 6C is a side view of an inner guide member according to another embodiment.

DETAILED DESCRIPTION OF THE ILLUSTRATED EMBODIMENTS

Figure 1:
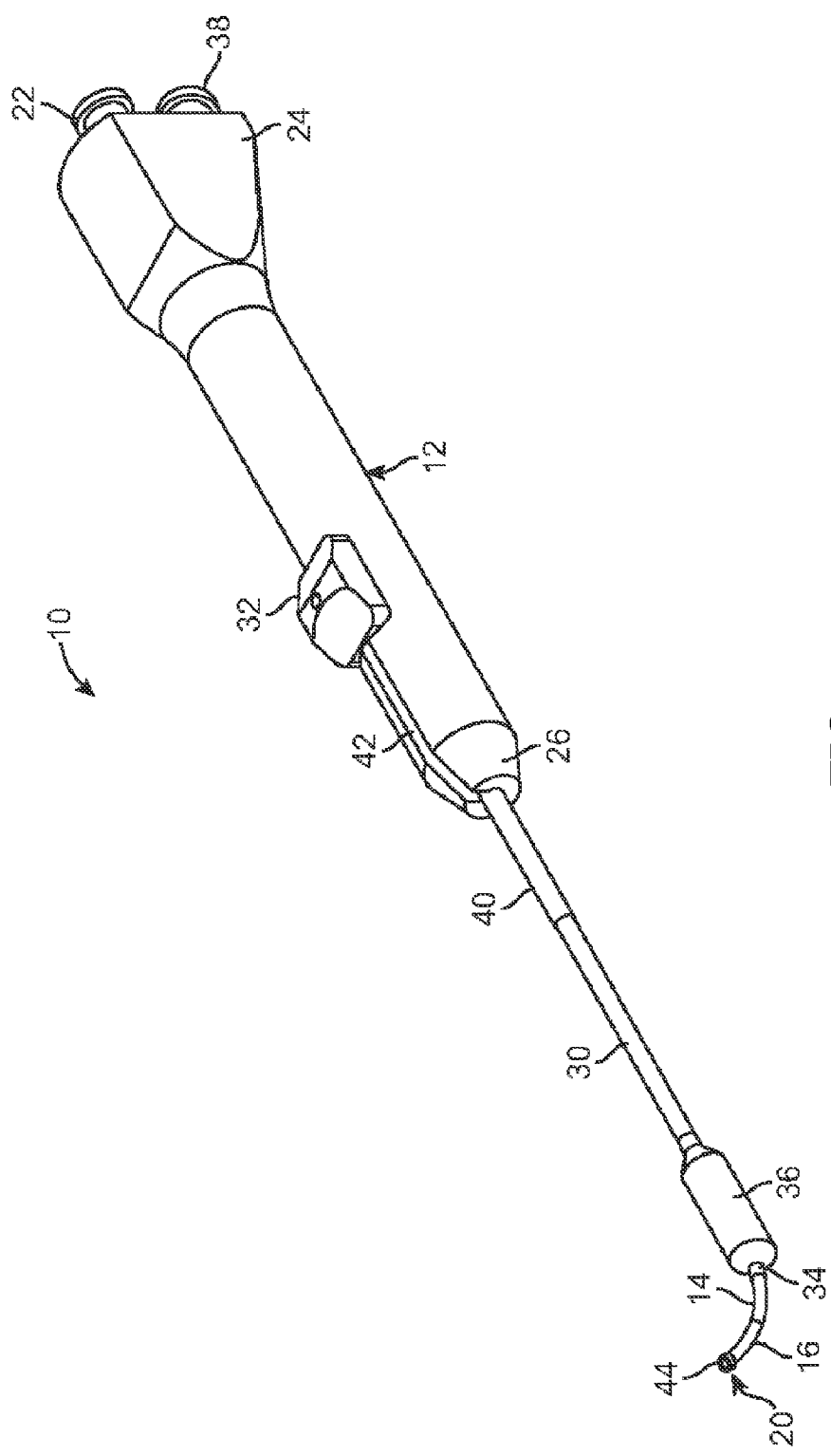
FIG. 1 illustrates a perspective view of a balloon dilation catheter according to one embodiment.

FIG. 1 illustrates one embodiment of a balloon dilation catheter 10 that is particularly suited for treatment of the outflow tract (frontal sinus ostium and frontal recess) of the frontal sinus of a subject. The balloon dilation catheter 10 includes a handle 12 that is configured to be gripped or otherwise manipulated by the operator. An elongate-shaped inner guide member 14 extends longitudinally from the handle 12 in a distal direction. The inner guide member 14 is formed of a suitably rigid material such as stainless steel hypotube. The inner guide member 14 projects or otherwise extends distally from the handle 12 for a pre-determined distance. The inner guide member 14 may be pre-shaped to have a curved distal portion 16 as is illustrated in FIGS. 1, 2A, 2B, 3A, 3B, 6A, 6B, 7, 8, and 9. For example, the nature and degree of the curved distal portion 16 may be configured to match with the frontal sinus outflow tract or frontal recess.

Alternatively, the inner guide member 14 may have some degree of malleability such that the user may bend or impart some desired shape or configuration to the distal end of the inner guide member 14. As explained herein in more detail, the inner guide member 14 may include an optional lumen 18 (best illustrated in FIG. 5A) that extends the length of the inner guide member 14. In particular, the inner guide member 14 and the contained lumen 18 may extend from a distal end 20 to a proximal end 21 (best seen in FIGS. 2B and 3B) that interfaces with a sealed arrangement with a port 22 disposed at a proximal end 24 of the handle 12. The port 22 may be configured with a conventional interface such as a Luer connector. The port 22 may be used as an aspiration port or a delivery port for fluids and/or medicaments, or for introduction of a guide wire.

Figure 2A:
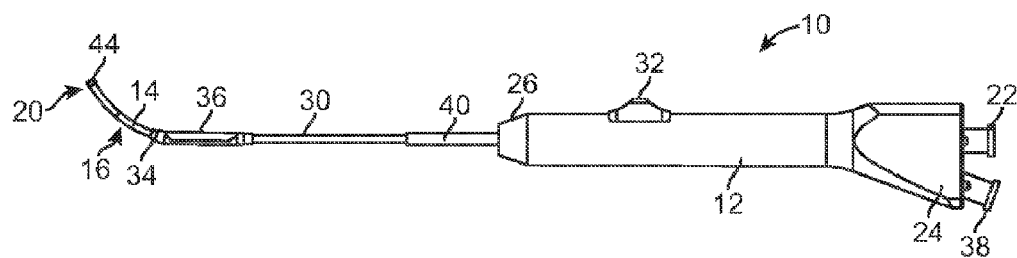
FIG. 2A illustrates a side view of a balloon dilation catheter of FIG. 1. The advancer knob is illustrated in the retracted, proximal position.
Figure 2B:
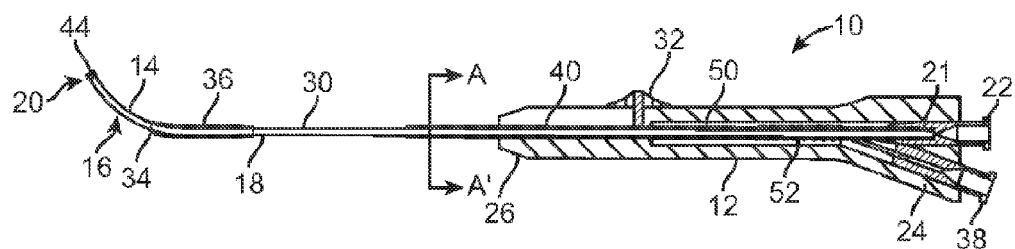
FIG. 2B illustrates a cross-sectional view of the balloon dilation catheter of FIG. 2A.

Still referring to FIG. 1, a shaft 30 is mounted about the periphery of the inner guide member 14. In particular, the shaft 30 is dimensioned to slide over the inner guide member 14 in response to actuation of an advancer knob 32 located on the handle 12. The advancer knob 32 is moveable along a slot 42 contained in a surface of the handle 12. A distal end 34 of the shaft 30 includes a balloon 36 that is configured to be selectively inflated or deflated as explained herein. During use, the inner guide member 14 is manipulated and advanced across or into the anatomical space of interest. The shaft 30 as well as the attached balloon 36 is illustrated in a retracted state in FIG. 1. While FIG. 1 illustrates the balloon 36 in an inflated state for better illustration, the balloon 36 is typically in a deflated state when the shaft 30 is in the proximal position as illustrated in FIGS. 2A and 2B. After the inner guide member 14 is properly positioned, the user actuates the advancer knob 32 by sliding the same in the distal direction which, in turn, advances the shaft 30 and balloon 36 in a distal direction over the pre-placed inner guide member 14. Once the balloon 36 is properly placed, the balloon 36 is inflated. Inflation of the balloon 36 is accomplished using an inflation device (not shown) that is coupled to a port 38 located at the proximal end 24 of the handle 12. One exemplary inflation device that may be used in connection with the balloon dilation catheter 10 is described in U.S. patent application Ser. No. 12/372,691, which was filed on 17 Feb. 2009, published as U.S. Pat. App. Pub. No. 2010/0211007, and is incorporated by reference as if set forth fully herein. Of course, other inflation devices may also be used. An inflation lumen 48 contained within the shaft 30 (described in more detail below), fluidically couples the port 38 to an interior portion of the balloon 36.

Still referring to FIG. 1, an optional support member 40 in the form of a tube may be located about the external periphery of a portion of the shaft 30 to impart further stiffness to the balloon dilation catheter 10. The particular length of the support member 40 may vary depending on the application and may extend along some or all or the shaft 30. The support member 40 may be made of a metallic material such as stainless steel hypotube that is secured to the shaft 30. The support member 40 may be welded or bonded along a length of the shaft 30. Generally, the support member 40 does not cover the helical portion (described in detail below) of the shaft 30 that is contained within the handle 12.

FIGS. 2A and 2B illustrate, respectively, side and cross-sectional views of the balloon dilation catheter 10 with the advancer knob 32 and thus balloon 36 in the proximal position. In actual use, as explained herein, the balloon 36 is typically in a deflated state when the advancer knob 32 is the proximal position as illustrated in FIGS. 2A and 2B. As best seen in FIG. 1, the advancer knob 32 is slidably disposed along a length of the handle 12 inside a slot 42. The advancer knob 32 is thus able to slide back and forth in the distal/proximal direction along the length of the slot 42. The slot 42 may incorporate a stop or the like (not shown) to prevent the balloon 36 from being advance too far along the length of the inner guide member 14. The length of the slot 42 may be varied in different devices to adjust the length at which the balloon 36 may be advanced. Generally, the slot 42 has a length within the range of about 1 inch to about 2 inches although other dimensions may fall within the scope of the invention.

As seen in FIG. 2B, the advancer knob 32 may be directly coupled to the support member 40 that is mounted on the shaft 30. Alternatively, the advancer knob 32 may be coupled directly to the shaft 30. The advancer knob 32 may be configured or otherwise shaped to enable a finger of the user (e.g., index finger or thumb) to easily advance or retract the knob 32 along the slot 42 contained in the handle 12.

Figure 3A:
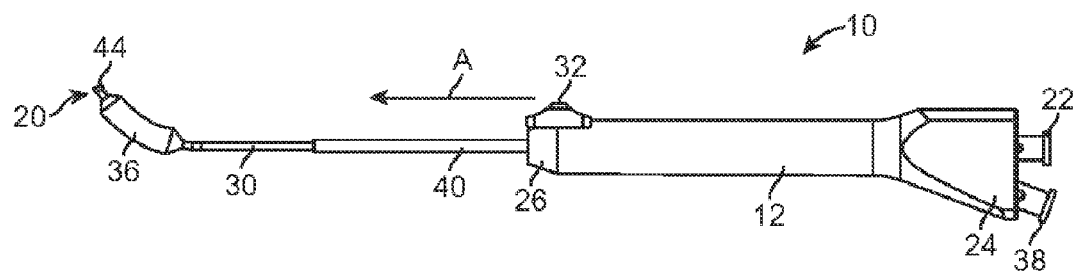
FIG. 3A illustrates a side view of a balloon dilation catheter of FIG. 1. The advancer knob is illustrated in the advanced, distal position.
Figure 3B:
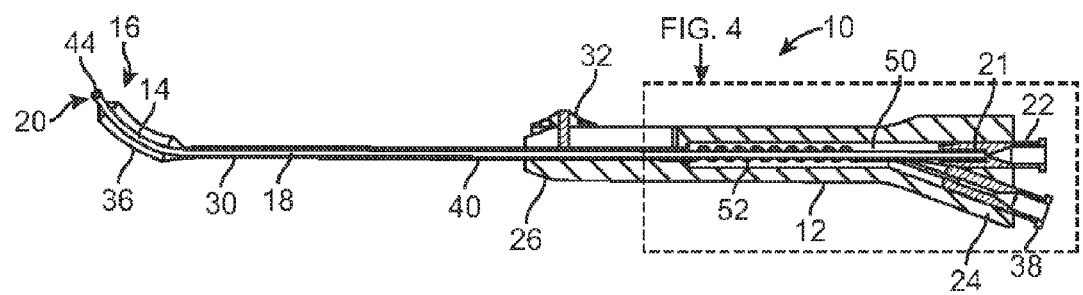
FIG. 3B illustrates a cross-sectional view of the balloon dilation catheter of FIG. 3A.

FIGS. 3A and 3B illustrate, respectively, side and cross-sectional views of the balloon dilation catheter 10 with the advancer knob 32 and thus balloon 36 in the distal position. Thus, unlike the configurations of FIGS. 2A and 2B, the advancer knob 32 is located at or near the distal end 26 of the handle 12. Advancement of the advancer knob 32 also slides the shaft 30 and attached balloon 36 in a distal direction (arrow A in FIG. 3A) along the inner guide member 14. The balloon 36 thus is positioned at or adjacent to the distal end 20 of the inner guide member 14. The balloon dilation catheter 10 may be designed such that the advancer knob 32 may be positioned at either the proximal or distal extremes as illustrated in FIGS. 2A, 2B, 3A, 3B. Alternatively, the advancer knob 32 may be positioned somewhere in between the two extremes. For example, the optimal position of the balloon 36 may be accomplished by sliding the advancer knob 32 some fraction (e.g., ¾) of the full distance of the slot 42.

Referring to FIGS. 2B and 3B, the inner guide member 14 of the balloon dilation catheter 10 extends from a distal end 20 to a proximal end 21 that terminates in a sealed interface with a port 22 disposed at a proximal end 24 of the handle 12. The inner guide member 14 optionally includes a lumen 18 disposed therein that may be used to provide aspiration functionality via an aspiration device (not shown) coupled to port 22. Aspiration functionality permits the removal of blood and other secretions. This makes it easier to visualize the placement of the balloon dilation catheter 10. The inner guide member 14 is advantageously rigid to enable the balloon dilation catheter 10 to be positioned without the need of a separate guiding catheter or guide wire in most, if not all, instances.

The inner guide member 14 may have a length of about 7 inches to about 11 inches from the distal end 20 to the proximal end 21 when loaded into the handle 12, although other dimensions may be used. The inner guide member 14 may be formed from stainless steel hypotube having an inner diameter in the range of about 0.019 inch to about 0.050 inch, and more preferably between about 0.036 inch and 0.040 inch, with a wall thickness within the range of about 0.005 inch to about 0.020 inch, and more preferably between about 0.008 inch to about 0.012 inch. The curved distal portion 16 of the inner guide member 14 may be formed right to the distal end 20 and may have a radius of curvature of about 0.25 inch to about 1.5 inch, and more preferably about 0.75 to about 1.25 inch.

The length of the inner guide member 14 that projects distally from the distal-most portion of the balloon 36 is about 0.5 inch to about 2.0 inch, and more preferably, about 0.8 inch to about 1.2 inch when the balloon 36 is in the fully retracted state (e.g., illustrated in FIGS. 2A and 2B). As seen in FIGS. 1, 2A, 2B, 3A, 3B, 6A-6C, 7-11, the distal end 20 of the inner guide member 14 may incorporate an optional bulbous tip 44 in order to make the distal end 20 more atraumatic. The bulbous tip 44 further serves to limit forward movement of the balloon 36 and attached shaft 30 when they are advanced distally. The outer diameter of the tip 44 is preferably between about 1 mm and about 3 mm.

The balloon 36 is mounted on the shaft 30 so as to form a fluidic seal between the two components. The balloon 36 may be bonded to the shaft using a weld, adhesive, or the like. Alternately, the balloon 36 may be secured to the shaft using a mechanical connection. Generally, any technique known to those skilled in the art may be used to secure to the balloon 36 to the shaft 30. Given that the balloon 36 is secured directly to the shaft 30, both structures are slidably mounted over the inner guide member 14. The balloon 36 generally takes on a cylindrical-shape when inflated. While not limited to specific dimensions, the inflated balloon 36 has a diameter within the range of about 3 mm to about 9 mm, and more preferably a diameter within the range of about 5 to about 7 mm when inflated. The length of the balloon 36 may generally fall within the range of about 10 mm to 25 mm although other lengths may be used. Both the shaft 30 and the balloon 36 are preferably formed of high strength but flexible polymeric materials such as polyamides (e.g., Nylon), PEBAX or the like. The balloon 36 may be "blow molded" to a relatively thin wall thickness, and capable of holding relatively high pressures from about 6 atmospheres to about 20 atmospheres of inflation pressure. The balloon 36 is inflated using a fluid which is typically a liquid such as water or saline.

Figure 4:
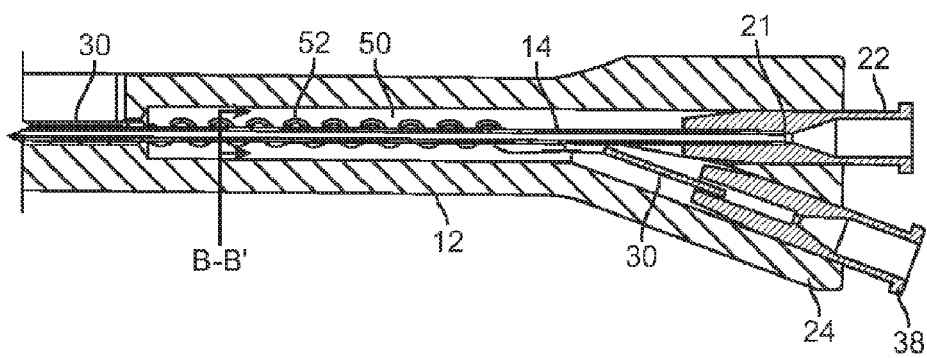
FIG. 4 is a cross-sectional view of the handle portion (dashed line portion) of FIG. 3B.

Referring now to FIG. 4, a magnified, cross-sectional view of a portion of the handle 12 is illustrated. At the proximal end 24 of the handle 12 are located ports 22, 38. The port 22 may be configured with a conventional interface such as a Luer connector or any other connector known to those skilled in the art. The port 22 may be integrally formed with the handle 12 or, alternatively, the port 22 may be a separate structure that is secured to the handle 12 during assembly. As seen in FIG. 4, the proximal end 21 of the inner guide member 14 forms a sealing arrangement with the port 22. As explained herein, the port 22 may be used as an aspiration port or a delivery port for fluids and/or medicaments.

FIG. 4 also illustrates port 38 which may be constructed in the same or similar manner as port 22 as described above. The port 38 is fluidically coupled to the inflation lumen 48 in the shaft 30. In this regard, inflation fluid from an inflation device (not shown) is able to pass through the port 38 and into the inflation lumen 48 of the shaft 30. The port 38 may be configured with a conventional interface such as a Luer connector. The fluid then is able to travel along the length of the shaft 30 via the lumen 48 where the fluid enters the interior of the balloon 36. The inflation fluid is thus able to inflate the balloon 36 upon actuation of the inflation device.

As best seen in FIG. 4, a portion of the handle 12 includes a recessed region 50 that receives both the inner guide member 14 and the shaft 30. In the recessed region 50 of the handle 12, the shaft 30 is helically wrapped around the outer periphery of the inner guide member 14 forming a helical portion 52. The helical portion 52 facilitates the distal advancement and proximal retraction of the shaft 30 and attached balloon 36 along the inner guide member 14 yet still maintains fluid communication with the port 38. The helical portion 52 of the shaft 30, which is located proximal to the advancer knob 32 is in the shape of a helix that wraps around the inner guide member 14 and is configured to elongate and contract upon movement of the advancer knob 32. FIG. 4 illustrates the state of the helical portion 52 after the advancer knob 32 has been advanced distally. Thus, in the extended state, the length of the helical portion 52 traverses much if not all of the recessed region 50. Contrast this with FIG. 2B which illustrates the helical portion 52 compressed to the proximal portion of the recessed region 50 because the advancer knob 32 is the in proximal position. Thus, the helical portion 52 is thus able to expand or compress much in the way that a spring does in response to a tensile or compressive load. One or both of the inner guide member 14 and the helical portion 52 of the shaft 30 may be optionally coated or lined with a lubricious coating to prevent the contact surfaces from any unwanted frictional binding or the like.

Figure 5A:
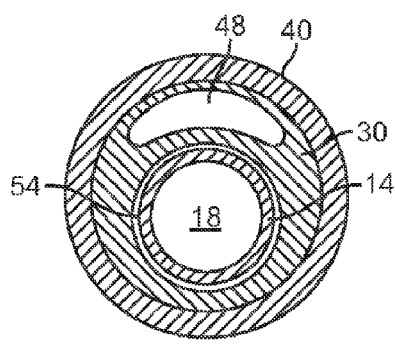
FIG. 5A is a cross-sectional view of the balloon dilation catheter taken along the line A-A' of FIG. 2B.
Figure 5B:
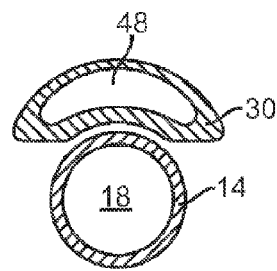
FIG. 5B is a cross-sectional view of the balloon dilation catheter taken along the line B-B' of FIG. 4.

The helical portion 52 of the shaft 30 may be formed by "skiving" away a portion of the shaft 30. FIG. 5A illustrates a cross-sectional view of the shaft 30, inner support guide 14, and support member 40 along the line A-A' of FIG. 2B. As seen in FIG. 2B, this area is distal to where the helical portion 52 of the shaft 30 is located. Referring now to FIG. 5A, the shaft 30 includes a rider lumen 54 that is dimensioned to have a diameter that is slightly larger than the outer diameter of the inner support guide 14. The rider lumen 54 thus enables the shaft 30 to advance and retract over the inner support guide 14 in a close-fit arrangement. The outer diameter of the shaft 30 may generally fall within the range of about 0.050 inch to about 0.110 inch or within the range of about 0.070 inch to about 0.100 inch. One or both of the exterior surface of the inner guide member 14 and the interior surface of the rider lumen 54 may be optionally coated with a lubricious coating to reduce frictional contact forces. FIG. 5B illustrates a cross-sectional view of the inner support guide 14 and the helical portion 52 of the shaft 30 taken along the line B-B' of FIG. 4. As seen in FIG. 5B, a portion of the shaft 30 that includes the rider lumen 54 is skived away. The result is that a single lumen (inflation lumen 48) remains in the shaft 30 that is helically wrapped about the inner support guide 14.

FIGS. 6A-6C illustrate various embodiments of an inner guide member 14. The inner guide member 14 may have a variety of shapes and configurations depending on the particular application or patient. The different shapes of the inner guide member 14 may be factory-formed in a particular shape and offered as a different model as fully assembled or, alternatively, the inner guide member 14 may be replaceable or modular elements that could slide inside the rider lumen 54 and inserted into the port 22 in a press-fit type sealing arrangement. In yet another alternative, the shapes could represent desirable shapes that a malleable inner guide member 14 could be formed into by the user to better fit a particular application or subject's anatomy.

FIG. 6A illustrates an inner guide member 14 that includes a curved distal portion 16 that terminates in a straight segment 46. In the embodiment of FIG. 6A, the curve in the curved distal portion 16 is pronounced and turns back on itself in the shape of a "U" in which the distal end 20 turns back in retrograde fashion. This embodiment may be useful to treat hard to reach ostia or other structures, e.g., the maxillary ostium or the infundibulum via a transnasal route, if the nasal anatomy will allow for a transnasal approach. While FIG. 6A illustrates a "U" shaped curve, other degrees of curvature are contemplated. FIG. 6B illustrates an inner guide member 14 according to another embodiment. In this embodiment, the curved distal portion 16 also terminates in a straight segment 46 although the radius of curvature is less pronounced. In this embodiment, the straight segment 46 may have a length within the range of about 8 mm to about 10 mm although other lengths may be used. It is believed that this embodiment is particularly suited for most frontal recess anatomy. FIG. 6C illustrates an embodiment in which the inner guide member 14 is substantially straight. This later embodiment may be particularly suited for treating the sphenoids of the subject, or straightforward frontal recess anatomy.

Figure 7:
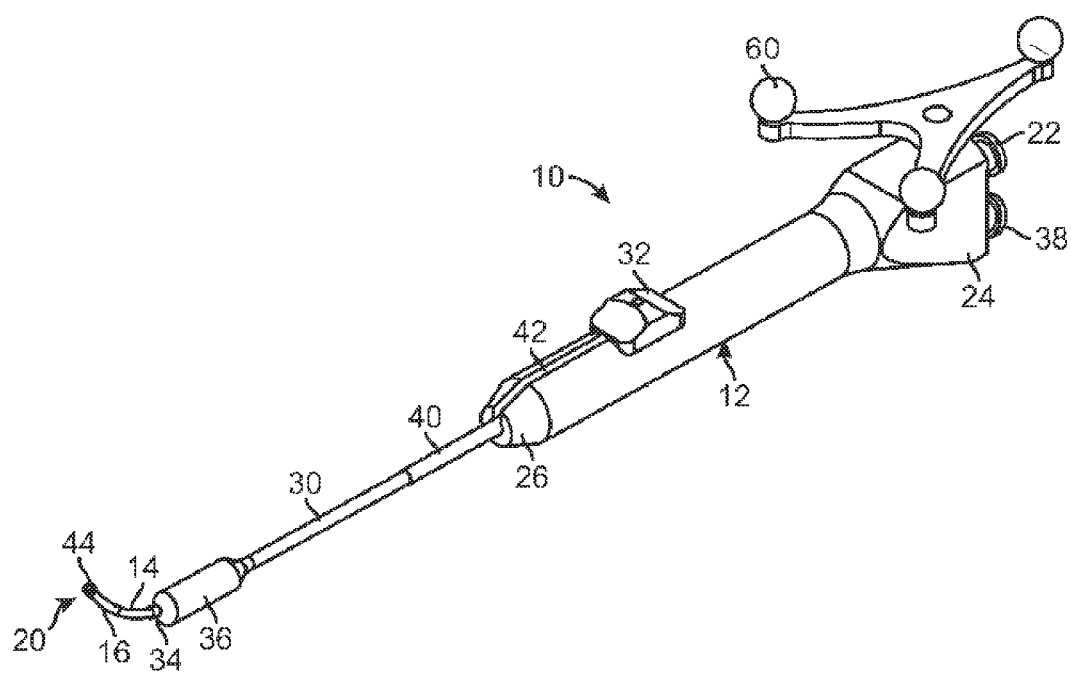
FIG. 7 illustrates a perspective view of a balloon dilation catheter according to another embodiment.

FIG. 7 illustrates a balloon dilation catheter 10 according to another embodiment. In this embodiment, a tracking element 60 is located on the handle 12 of the balloon dilation catheter 10. The tracking element 60 may include an antenna, transmitter, optical reflectors, or the like that communicates a wireless signal that is then received and processed to determine the orientation and/or positioning of the balloon dilation catheter 10. In certain embodiments, more than one tracking element 60 may be disposed on the balloon dilation catheter 10. Data regarding the orientation and/or positioning of the balloon dilation catheter 10 may then be processed and displayed on the display for viewing by the physician. For example, image guided surgery is becoming increasingly commonplace, permitting physicians to review real time actual or virtual images of a particular device within a subject during a surgical procedure.

For example, U.S. Pat. Nos. 5,391,199 and 5,443,489, which are incorporated by reference, describe a system wherein coordinates of an intrabody probe are determined using one or more field sensors such as, Hall effect devices, coils, or antennas that are carried on the probe. U.S. Patent Application Publication No. 2002-0065455, which is also incorporated by reference, describes a system that is capable of generating a six-dimensional position and orientation representation of the tip of a catheter using a combination of sensor and radiation coils. U.S. Patent Application Publication No. 2008-0269596, which is also incorporated by reference, describes yet another monitoring system that has particular applications in orthopedic procedures. Commercial systems such as the LANDMARX Element (Medtronic Xomed Products, Inc., Jacksonville, Fla.) are available for use in conjunction with ENT procedures.

In the embodiment of FIG. 7, the tracking element 60 permits accurate tracking of the distal end 20 of the balloon dilation catheter 10 such that an image of distal portion of the balloon dilation catheter 10 may be superimposed on a patient's anatomical imagery. For example, a previously conducted computed tomography (CT) scan of the patient may be used to generate a visual image of the patient's anatomical regions of interest. Based on the location of the tracking element 60, an image guided surgery (IGS) system can then superimpose an image of the balloon dilation catheter 10 onto the image to better enable the physician to manipulate and orient the balloon dilation catheter 10.

Other commercial systems may also be used in connection with the balloon dilation catheter 10 illustrated in FIG. 7. For example, the INSTATRAK 3500 Plus—ENT from GE Healthcare, Chalfont St. Giles, United Kingdom may be integrated and/or used with the balloon dilation catheter 10. The use of CT guidance to position the balloon dilation catheter 10 is preferred because the device may be positioned by the operator with just a single hand, while viewing the CT image interface (e.g., display) at the same time the handle 12 is manipulated. Optionally, the balloon dilation catheter 10 may be initially positioned using an endoscope or other visualization tool. For instance, a conventional "Hopkins rod" endoscope (not shown) may be manipulated alongside the balloon dilation catheter 10 to aid in placement.

Figure 8:
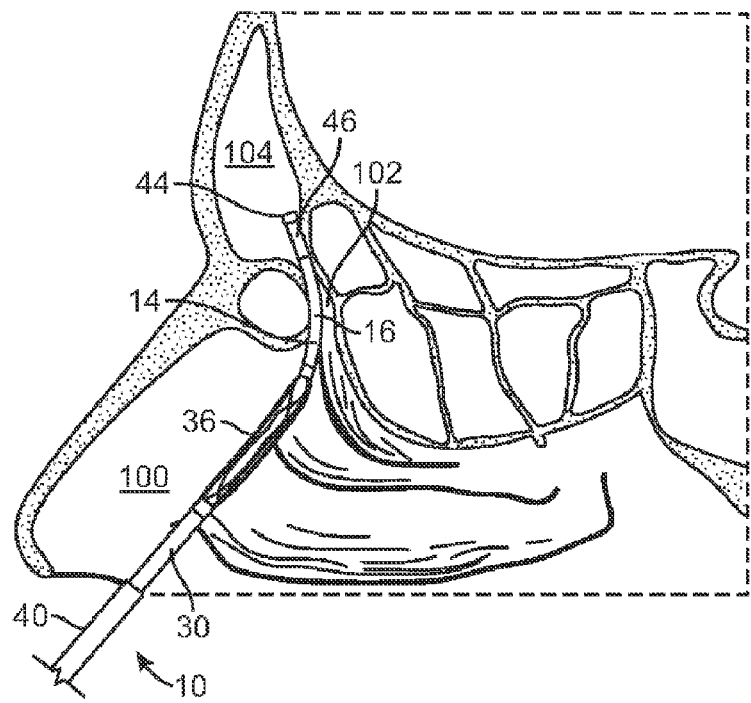
FIG. 8 illustrates a cross-sectional view of the frontal sinus of a subject with the inner guide member of the balloon dilation catheter being advanced into the subject's frontal recess.

FIGS. 8-12 illustrate various cross-sectional views (sagittal plane) of the frontal sinus of a subject undergoing treatment with a balloon dilation catheter 10. The cross-sectional views illustrate the nasal passageway 100, the frontal recess 102, and the frontal sinus cavity 104. Referring to FIG. 8, the balloon dilation catheter 10 is inserted into the nasal passageway 100 with the advancer knob 32 in the retracted position (e.g., as illustrated in FIG. 1, 2A, 2B) such that the shaft 30 and balloon 36 are also retracted proximally. In addition, the balloon 36 is in a deflated state as seen in FIG. 8. The curved portion 16 of the inner guide member 14 is then positioned within the frontal recess 102 of the subject as seen in FIG. 8. This positioning of the inner guide member 14 may be accomplished under endoscopic visualization using a conventional endoscope such as a Hopkins rod-type endoscope that is positioned alongside the balloon dilation catheter 10. Alternatively, the inner guide member 14 may be positioned using IGS techniques that track the position of the balloon dilation catheter 10 using one or more tracking elements 60 as illustrated, for instance, in the embodiment of FIG. 7. For instance, the inner guide member 14 may be advanced under guidance from CT imaging.

Figure 9:
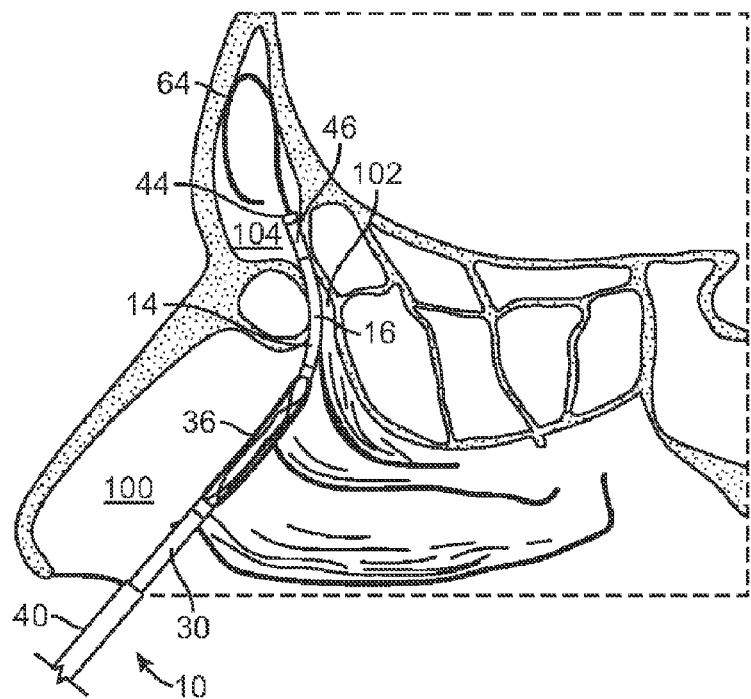
FIG. 9 illustrates a cross-sectional view of the frontal sinus of a subject with the inner guide member of the balloon dilation catheter being positioned in the subject's frontal recess. A guide wire is shown advanced through the catheter and into the subject's frontal sinus cavity.

Referring now to FIG. 9, confirmation of accurate positioning of the inner guide member 14 within the frontal recess 102 may be accomplished by placement of a fluoroscopically visible guide wire 64 through the lumen 18 of the inner guide member 14. The guide wire 64 may be inserted into the lumen 18 via the port 22. Under fluoroscopic visualization, the guide wire 64 can be seen to advance into the frontal sinus cavity 104 once the inner guide member 14 is positioned properly within the frontal recess 102. If the guide wire 64 does not advance into the frontal sinus cavity 104, the balloon dilation catheter 10 is re-positioned and confirmation is subsequently attempted. As an alternative to a fluoroscopically visible guide wire 64, the guide wire 64 could be a light emitting guide wire such as that disclosed in U.S. Patent Application Publication No. 2007-0249896, which is incorporated by reference herein. Of course, the guide wire 64 is optional as the inner guide member 14 may be placed without the aid or need for the same. Alternatively, the guide wire 64 could be positioned in the frontal sinus initially, prior to placement of the balloon catheter 10.

Figure 10:
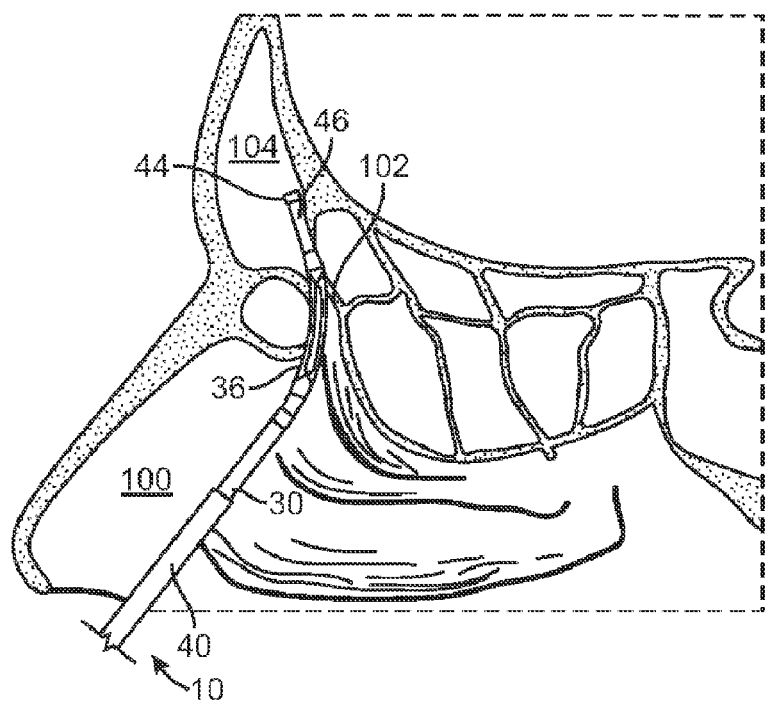
FIG. 10 illustrates a cross-sectional view of the frontal sinus of a subject with the balloon (in a deflated state) and shaft being advanced into the subject's frontal recess.
Figure 11:
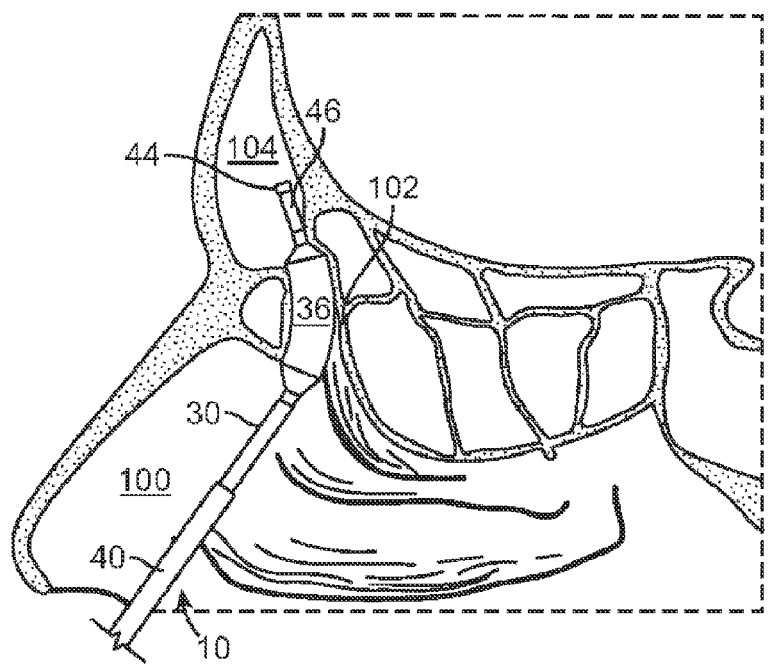
FIG. 11 illustrates a cross-sectional view of the frontal sinus of a subject with the balloon of FIG. 10 in an inflated state to thereby widen and remodel the frontal recess.

Now referring to FIG. 10, once the curved portion 16 of the inner guide member 14 is properly positioned, the advancer knob 32 is advanced in the distal direction (arrow A of FIG. 3A) thereby advancing the shaft 30 and attached balloon 36 into the frontal recess 102. This is illustrated in FIG. 10. After the balloon 36 is positioned in the frontal recess 102, the balloon 36 is inflated as illustrated in FIG. 11. Inflation is accomplished by coupling an inflation device (not shown) to the port 38. The inflation device may include a syringe or the like that is depressed to infuse a fluid into the inflation lumen 48 which then passes into the interior of the balloon 36 to effectuate expansion of the balloon 36 to the state illustrated in FIG. 11. Pressures typically used to accomplish widening or remodeling of the frontal recess 102 are within the range of about 3 atmospheres to about 12 atmospheres. The balloon 36 may be inflated only a single time or, alternatively, the balloon 36 may be inflated, deflated, and inflated again a plurality of times in order to achieve the desired degree of widening. Each inflation step may be performed after positioning the balloon 36 in a different position within the frontal recess 102.

Figure 12:
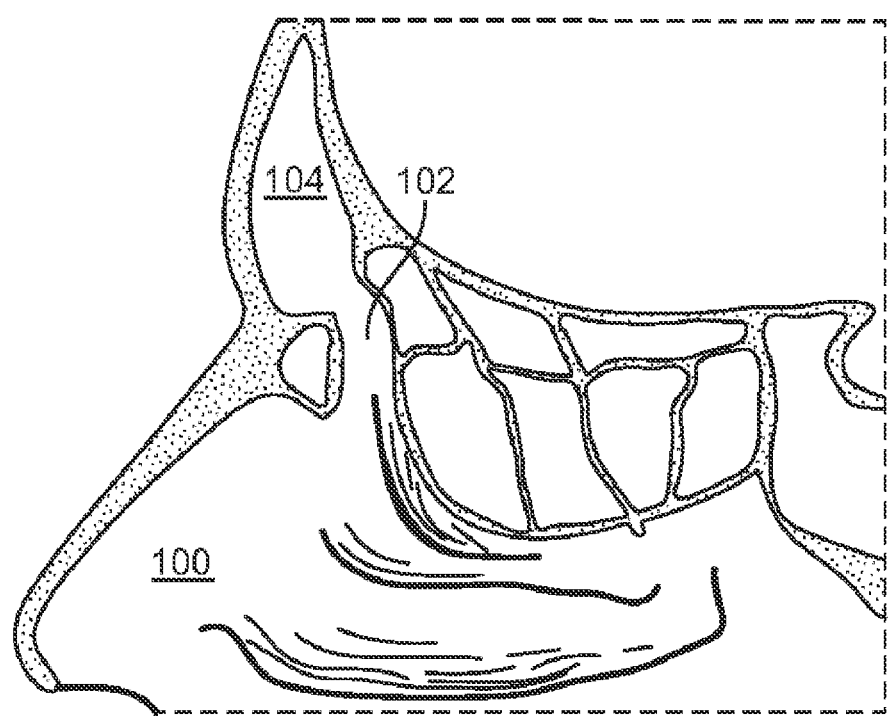
FIG. 12 illustrates a cross-sectional view of the frontal sinus of a subject after the frontal sinus has been widened and the balloon inflation catheter withdrawn.

After the frontal recess 102 has been widened or otherwise remodeled, the balloon 36 is deflated and removed as illustrated in FIG. 12. The widened frontal recess 102 illustrated in FIG. 12 is believed to restore the drainage and aeration function and health of the frontal sinus cavity 104. Deflation of the balloon 36 is accomplished by reducing the fluid pressure within the interior of the balloon 36. For example, the plunger of a syringe or the like that is fluidically coupled to the port 38 may be withdrawn to remove fluid from the interior of the balloon 36. The balloon dilation catheter 10 can then be withdrawn proximally from the nasal passageway 100.

In certain patients, treatment of one or both frontal sinuses 104 as described above may be adequate. In other patients, additional sinuses may need to be treated, particularly the maxillary and/or anterior ethmoid sinuses. In such patients, a combination procedure may be well suited. The maxillary and/or anterior ethmoid sinuses can be treated with a system such as described in U.S. Pat. No. 7,520,876 and U.S. Patent Application Publication No. 2008-0172033, commercially available as the FinESS system by Entellus Medical, Inc. of Maple Grove, Minn. Alternatively, other sinuses could be treated more conventionally using surgical techniques such as, for instance, functional endoscopic sinus surgery (FESS).

Also, the sphenoid and/or maxillary sinus outflow tracts could be dilated with the embodiment of the balloon catheter 10 described above. It is also contemplated that the balloon catheter 10, particularly the embodiment of FIG. 7 with a suitable IGS device is incorporated, and with an appropriate shape for the inner support member 14, preferably straight as illustrated in FIG. 6C, could be used to dilate the maxillary sinus outflow tract via the canine fossa route. Suitable access tools are described in co-pending U.S. patent application Ser. No. 12/038,719, which was published as U.S. Patent Publication 2009-0216196 and is incorporated by reference herein. This could be performed without need for additional endoscopic visualization, permitting treatment through a relatively small diameter access passageway into the sinus cavity in the region of the canine fossa. A small endoscope (not shown) could be utilized, if desired, through the lumen 18 of the inner support member 14 to further aid in visualization of the maxillary sinus outflow tract.

In some embodiments, the invention includes the use of a light source to help a practitioner identify portions of, or confirm a location within, a sinus cavity or sinus cavity drainage pathway. For example, in some embodiments, a distal portion of a lighted instrument (e.g., a lighted guidewire, a lighted endoscope, or a lighted probe) is inserted into a subject via a transnasal route and directed into a space or body lumen that a practitioner suspects is a part of the frontal drainage pathway that leads to a frontal sinus cavity. The practitioner directs the lighted distal end of the instrument into the suspected pathway and gently advances the instrument further into the body lumen. If the lumen leads to a frontal sinus cavity, the light from the distal tip will travel through the bone and tissue walls of the cavity and provide a transdermal or transcutaneous illumination pattern visible to the practitioner. In this way, the practitioner can confirm that the suspected body lumen is a part of the frontal drainage pathway and does in fact lead to a frontal sinus cavity. Manipulation of the instrument (e.g., rotation) will move the illumination pattern, further confirming the positioning the instrument in the frontal recess. Once confirmed as part of the drainage pathway, the practitioner can use the other embodiments of this invention discussed above to dilate all or parts of the pathway. Typically, the lighted instrument would be removed from the frontal recess prior to the placement of any embodiment of the invention used to dilate all or parts of the pathway.

In another example, in some embodiments of the invention, a distal portion of a lighted instrument is used to confirm that a given location is within the maxillary sinus cavity. The practitioner directs the lighted distal end of the instrument to the location and looks for a visible transdermal or transcutaneous illumination pattern (e.g., an illumination pattern on the roof of the mouth or through the skin near the cheekbone). Once the pattern is observed, the practitioner then knows the given location is within the maxillary sinus cavity. If the pattern is not observed, the practitioner then knows the given location is unlikely to be within the maxillary sinus cavity.

In some embodiments, the lighted instrument is a lighted probe, such as device 1300 as illustrated in FIGS. 13-16. FIG.

Figure 14:
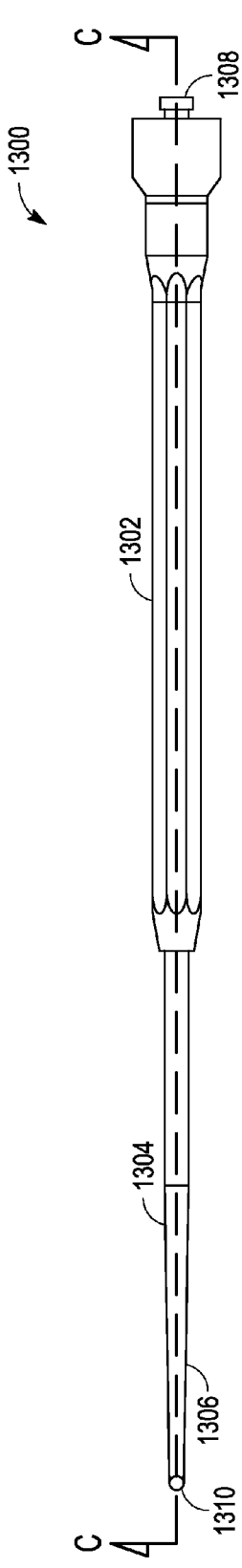
FIG. 14 illustrates a top view of a lighted probe device.
Figure 15:
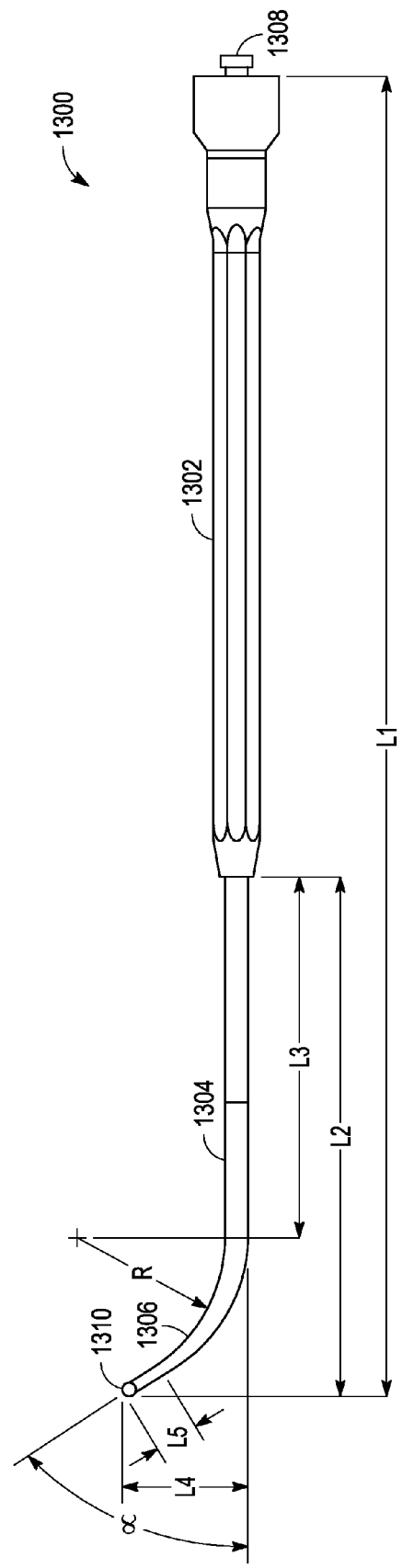
FIG. 15 illustrates a side view of a lighted probe device.
Figure 16:
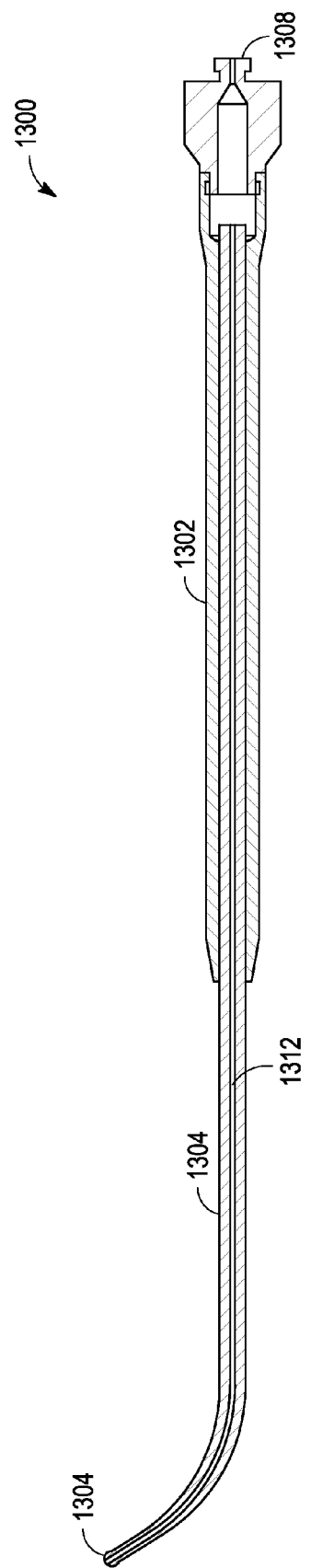
FIG. 16 illustrates a cross-sectional view of the lighted probe device taken along line A-A of FIG. 14.

13 illustrates a perspective view of the entire length of device 1300, while FIGS. 14 and 15 illustrate top and side views of device 1300, respectively. FIG. 16 illustrates a cut-away side view of device 1300 along lines C-C of FIG. 14.

Lighted probe device 1300 includes a handle portion 1302 forming a proximal portion of device 1300. Handle portion 1302 is configured to be gripped or otherwise manipulated by the operator. Attached to handle portion 1302 is an elongate-shaped probe member 1304 formed from a suitably rigid material such as a stainless steel hypotube. Probe member 1304 projects or otherwise extends distally from handle 1302. Probe member 1304 is pre-shaped to have a curved distal portion 1306. The nature and degree of curvature of probe member 1304 can be configured to match with the frontal sinus outflow tract or frontal recess. In some embodiments, probe member 1304 has some degree of malleability such that a user may bend or impart some desired shape or configuration to the distal end of probe member 1304.

Device 1300 defines a light-fiber bundle lumen 1312 that extends along its length, from proximal end 1308 to distal tip 1310. Lumen 1312 contains a light-fiber bundle that, during use, directs light from a light source connected at proximal end 1308 and out through distal tip 1310 of device 1300. In some embodiments, lumen 1312 contains a single light-fiber (e.g., a 30 micron 0.44 NA illumination fiber or a 0.55-0.66 NA light fiber) while in other embodiment lumen 1312 contains multiple light-fibers. The light fiber may, for example, be able to conduct a light powerful enough to produce a 15,000 lux or greater illuminance at distal tip 1310.

In some embodiments, the light-fiber or fiber bundle may be adhered to the inside walls of lumen 1312 using an epoxy (e.g., EP42HT-CLEAR available from Master Bond, Inc. of Hackensack, N.J.). In other embodiments, the light-fiber or fiber bundle may be removably inserted or removably secured within lumen 1312 such that the light-fiber or fiber bundle can be removed from device 1300 at some point during use. For example, during use, a practitioner of the invention can insert the light fiber or fiber bundle into lumen 1312, use the lighted probe device to identify portions of the sinus cavity or sinus cavity drainage pathway or to confirm a location within the nasal or sinus system, remove the light-fiber or fiber bundle while leaving the body portion of device 1300 in place, and then use the lumen of device 1300 to guide other devices to a desired location. Alternatively, or in addition, the lumen of device 1300 could be attached to a vacuum source or a fluid could be directed through the lumen 1300 (thereby allowing a practitioner to apply suction or deliver water and/or a medicament to a desired location within a sinus system before, during, or after use of the light-fiber or fiber bundle). In a further example, the light-fiber or fiber bundle can be removed while leaving the remainder of device 1300 in a desired or confirmed location, thereby providing a visual guide along side of which a practitioner can guide other devices (e.g., a balloon dilation device) to the desired or confirmed location. In some embodiments, the invention includes a removable light-fiber or fiber bundle that includes an atraumatic tip (e.g., a spherical ball tip).

Figure 13:
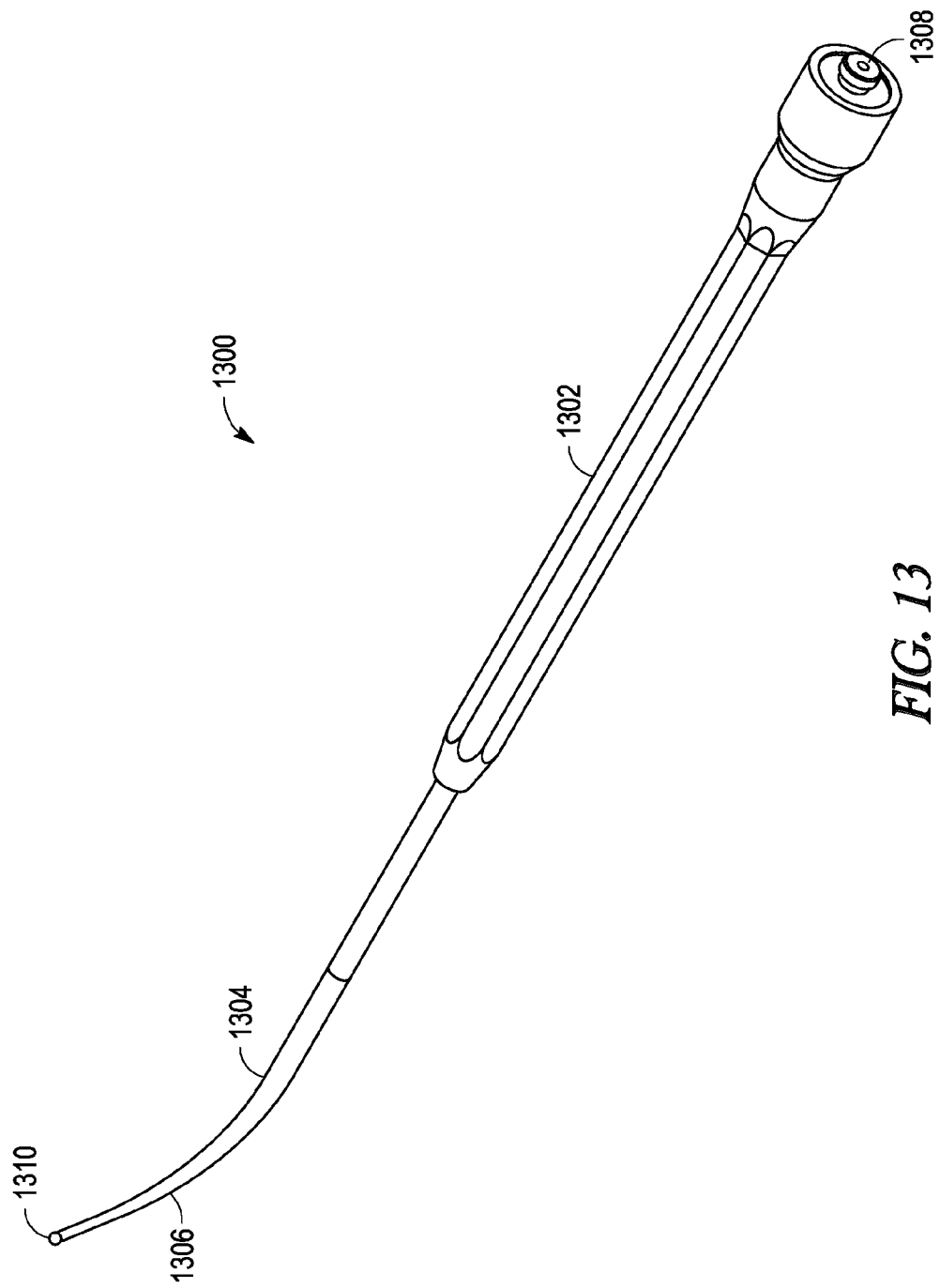
FIG. 13 illustrates a perspective view of a lighted probe device.

In some embodiments, device 1300 may be attached or connected to a light source at proximal end 1308 and the light source directs light into and through the fiber bundle in lumen 1312 and out distal tip 1310. Distal tip 1310 can include an atraumatic tip (as best illustrated in FIG. 13). The specific size and dimensions of the lighted probe can be varied in order to adapt the device for specific indications or uses. FIG. 15 illustrates some of the dimensions of lighted probe 1300, including overall length $L_1$; lengths $L_2$, $L_3$, $L_4$, and $L_5$; angle $\alpha$, and radius of curvature R.

The below Table 1 lists the numeric range of values that those dimensions can take depending upon the specific design parameters for a given embodiment of a lighted probe.

TABLE 1

| Dimension | Quantitative Value |
| --- | --- |
| Length $L_1$ | ~6 to ~8.5 inches |
| Length $L_2$ | ~1.5 to ~4 inches |
| Length $L_3$ | ~0.750 to ~3 inches |
| Length $L_4$ | ~0.1 to ~1.2 inches |
| Length $L_5$ | ~0.170 to ~0.250 inches |
| Angle $\alpha$ | ~0 to ~120 degrees |
| Radius of curvature R | 0.125 and 0.850 inches |

In some embodiments of the invention, the lighted probe is sized and dimensioned to match or access the frontal sinus outflow tract or frontal recess of a typical patient population, while in other embodiments the probe is sized and dimensioned to match or access the maxillary and/or sphenoid sinus outflow tracts and/or cavities. For example, a lighted probe having an Angle $\alpha$ of about zero degrees (essentially a straight probe) would be particularly useful for accessing the sphenoid sinus spaces. In some preferred embodiments, angle $\alpha$ is in a range of from about 28 degrees to about 88 degrees while the other dimensions angle $\alpha$ fall within the ranges listed in Table 1. In an especially preferred embodiment, length $L_1$ is about 7.067 inches, length $L_2$ is about 2.777 inches, length $L_3$ is about 1.930 inches, length $L_4$ is about 0.639 inches, length $L_5$ is about 0.210 inches, an angle $\alpha$ is about 58 degrees, and a radius of curvature R of about 0.850 inches. In another especially preferred embodiment, length $L_1$ is about 6.886 inches, length $L_2$ is about 2.616 inches, length $L_3$ is about 1.931 inches, length $L_4$ is about 0.763 inches, length $L_5$ is about 0.210 inches, an angle $\alpha$ is about 78 degrees, and a radius of curvature R of about 0.630 inches. In another especially preferred embodiment, particularly suited for use in the maxillary sinus cavities and outflow tract, angle $\alpha$ is between about 60 and about 120 degrees, the radius of curvature R is between 0.125 and 0.50 inches, and length $L_4$ is between about 0.150 and 0.750 inches.

In some embodiments, the atraumatic ball tip of distal tip 1310 has a diameter in the range of between about 0.5 millimeters to about 2.5 millimeters, while in some specific embodiments the atraumatic ball tip has as diameter of about 0.060 inches.

In some embodiments, probe member 1304 has an inner wall diameter of between 0.0195 inches and 0.0225 inches and an outer wall diameter of between 0.1089 inches and 0.1092 inches. In some embodiments, the distal portion of probe member 1304 has an outer wall diameter that tapers gradually to a narrowed distal tip.

Prior or after use, the lighted probe can be sterilized via autoclaving, EtOH sterilization, or gamma irradiation.

Figure 17:
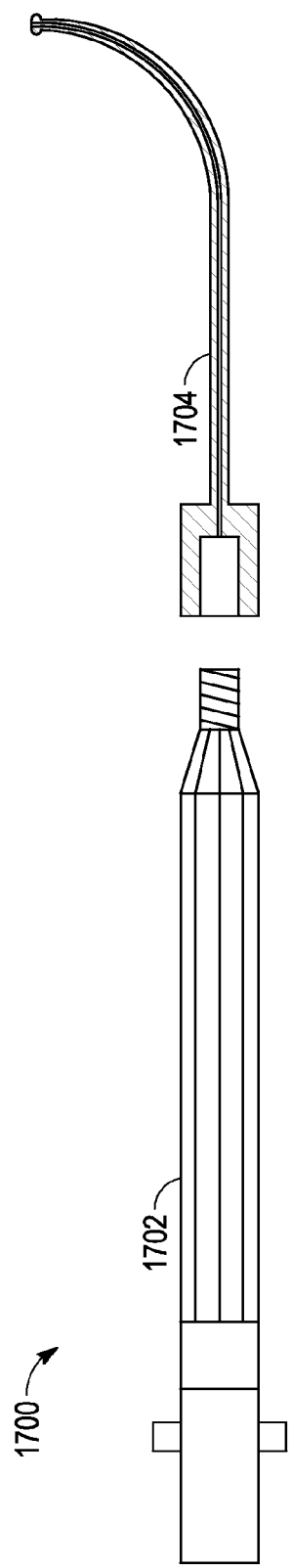
FIG. 17 illustrates an exploded side view of a light source.

In some embodiments, the invention includes the use of a light source having a distal portion that can be detached. FIG. 17 illustrates such an embodiment as light source 1700. Light source 1700 includes handle portion 1702 and detachable distal portion 1704. In some embodiments, one of the two portions (e.g., the handle portion) can be made of relatively resilient materials so that it can be sterilized and reused many times while the other portion is made of more economical materials so that it can be disposed of after one use. In further embodiments, the handle portion can be made to accommodate a wide variety of different second portions (e.g., differently shaped detachable distal portions).

Frequently, whenever two light-conducting elements join at a juncture, heat is generated when light crosses the juncture due to imperfections in the juncture. This is especially true when the juncture is between light-conducting elements made of disparate materials (e.g., one made of glass fiber and a second made of a polymeric fiber). In some cases, the heat generated can be quite substantial and can damage the light-conducting elements or burn an operator. In some embodiments, this invention includes a connector used to connect a light source of the invention with a light cable. The connector provides a juncture between the light source and the light cable that can reduce the amount of heat generated, and/or dissipates generated heat, more effectively and safely than if the light source and light cable were joined without the connector.

Figure 18:
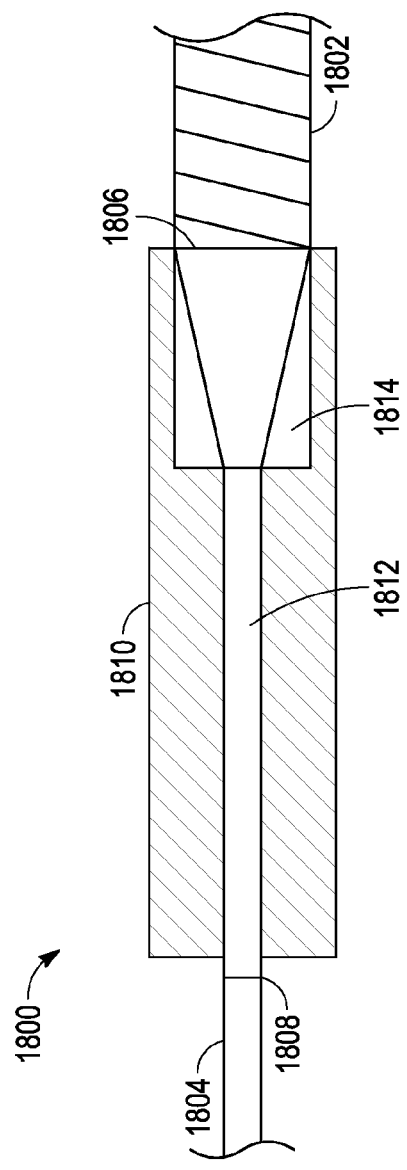
FIG. 18 illustrates a cross-sectional side view of a connector.

FIG. 18 illustrates such an embodiment as connector 1800. Connector 1800 can be attached on one side to light cable 1802 to form juncture 1806 and on the other side to proximal end 1804 of the light fiber or fiber bundle of a light source of the invention to form juncture 1808 (for clarity, only the fiber bundle of a light source of the invention is illustrated in FIG. 18). Connector 1800 includes housing 1810 that can be formed of a material that dissipates heat quickly (e.g., aluminum). Housing 1810 defines an inner lumen portion that contains a light-conducting element 1812 (e.g., a glass fiber or fiber bundle) and light taper 1814. Light taper 1814, together with light cable 1802, forms juncture 1806. Light-conducting element 1812, together with proximal end 1804, forms junction 1808.

In use, light is transmitted across junction 1806 from light cable 1802 to light taper 1814, where it is concentrated and focused into glass fiber 1812. The light then travels along glass fiber 1812, across junction 1806, and into proximal end 1804. While some amount of heat may be generated at junctions 1806 and 1808, the heat is easily dissipated by housing 1810, thereby preventing a undesirable amount of heat from building up in the assembly components.

Figure 19A:
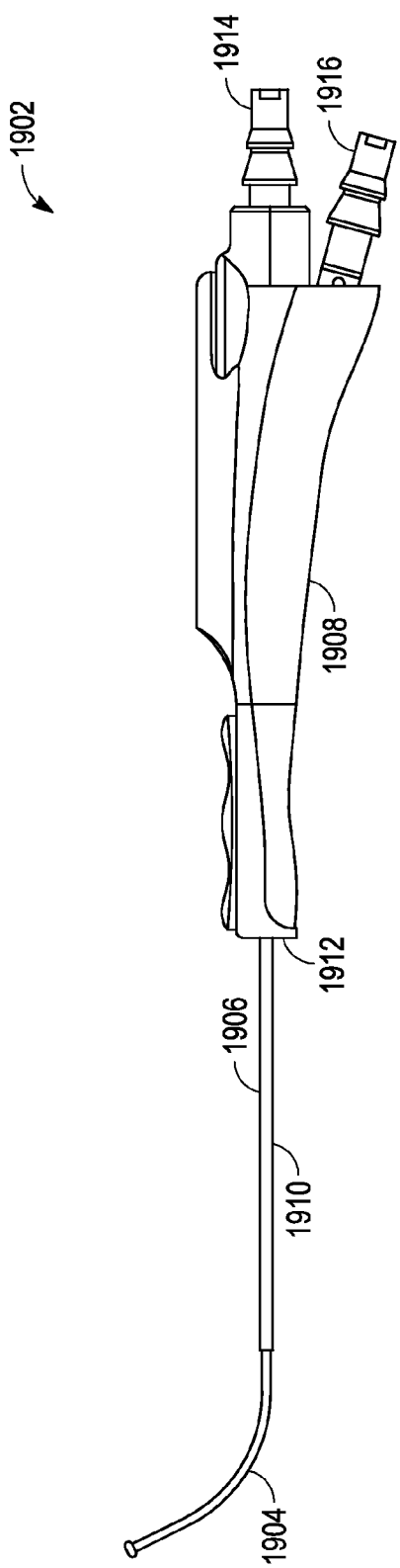
FIG. 19A illustrates a perspective view of a guide catheter.
Figure 19B:
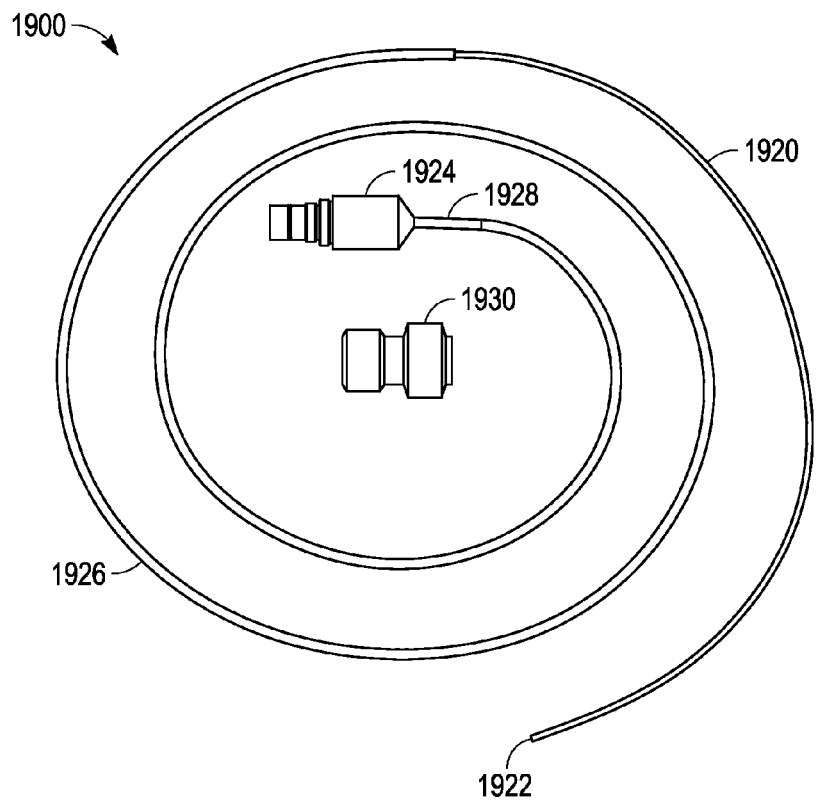
FIG. 19B illustrates a photographic view of a removable light-fiber light source and tuohy-borst connector.
Figure 19C:
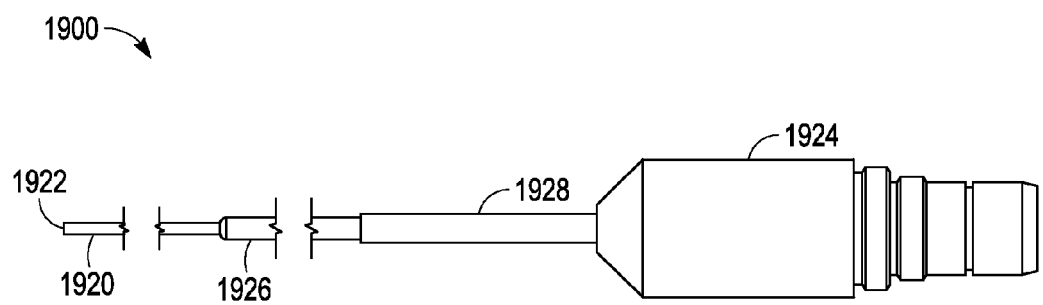
FIG. 19C illustrate a perspective side view of portions of a removable light-fiber light source.

FIGS. 19A-19C illustrate various aspects of an embodiment of the invention that includes a light source device that have a removable light-fiber 1900 and guide catheter 1902.

Guide catheter 1902 includes hypotube 1906 having malleable distal end 1904 and rigid distal portion 1910. Hypotube 1906 extends through handle 1908, with malleable distal end 1906 and a distal portion of rigid distal portion 1910 extending from distal end 1912 of handle 1908. Hypotube 1906 defines a lumen extending from proximal portion 1914 to distal tip of malleable distal end 1912. Second proximal portion 1916 defines a second lumen that joins together and is in fluid communication with the lumen defined by hypotube 1906.

Removable light-fiber 1900 is illustrated in FIGS. 19B and 19C, with portions of the length of light-fiber 1900 omitted from FIG. 19C for clarity. Light-fiber 1900 includes a length of single light-conducting fiber 1920 that extends from distal tip 1922 to proximal light connector 1924. A proximal portion of light-fiber 1900 includes protective sheath 1926 of polymeric material overlying light-fiber 1920 and protective sheath 1928 of polymeric or metallic material overlying a proximal portion of protective sheath 1926. FIG. 19B also illustrates tuohy-borst connector 1930.

In use, distal tip 1922 of light-fiber 1900 is directed into proximal portion 1914 of catheter 1902, through the lumen defined by hypotube 1906, and to the distal tip of malleable distal end 1904. A light source is connected to proximal light connector 1924 so that light is conducted along light-fiber 1920 and projected out from distal tip 1922. Light-fiber 1900 can be secured to catheter 1902 using connector 1930. In this way, the light conducting light-fiber 1900 is mounted within catheter 1902 such that the light from distal tip 1922 emanates from the distal end of catheter 1902. Once assembled to light-fiber 1900, catheter 1902 can be used to probe a sinus system and confirm, via transdermal illumination, when the position of the distal end of catheter 1902 is within a maxillary or frontal sinus structure. Catheter 1902 can also be used light a flashlight to illuminate sinus structures for viewing structures within the sinus system with an endoscope. Once viewing or transdermal confirmation has been completed, a user may withdraw both catheter 1902 and light-fiber 1900 from the sinus system or, alternatively, may remove light-fiber 1900 leaving catheter 1902 within the sinus system. Fluid (e.g., saline) or suction sources may be secured to second proximal portion 1916 in order to direct fluid from the distal end of malleable distal end 1904 or suction material into and through catheter 1902.

In some embodiments of the invention, a portable light source may be used and attached to the light-conducting devices described herein (e.g., device 1300 or light-fiber 1900). The portable light source may include a battery-powered LED light source.

In some embodiments of the invention, light of various wavelengths may be directed through the light-conducting devices described herein (e.g., device 1300 or light-fiber 1900). Red or infrared light tends to pass through blood and tissue more easily than light of other spectrums, so use of red light can be desirable when performing transdermal illumination. Hence, in some embodiments of the invention, a red light may be used with the light-conducting devices described herein when the devices are used to illuminate transdermally while a white light may be used when the devices are used to view structures with an endoscope. In some embodiments of the invention, a portable light source having two dissimilar colors of light (e.g., white and red) is used with the light-conducting devices described herein, with the user toggling the light source between the two colors as desired during use.

While embodiments of the present invention have been shown and described, various modifications may be made without departing from the scope of the present invention. The invention, therefore, should not be limited, except to the following claims, and their equivalents.

What is claimed is:

1. A method of treating a sinus cavity of a subject using a balloon dilation catheter, the method comprising:
   providing a lighted instrument and illuminating at least a portion of the sinus cavity;
   providing a balloon dilation catheter that includes
      a handle having a stationary inflation port located in a proximal end of the handle,
      an inner guide member secured to the handle and extending distally from a distal end of the handle a predetermined distance,
      a balloon catheter slidably mounted on the inner guide member and including an inflatable balloon coupled to the stationary inflation port with an inflation lumen,
      a shaft coupled to the balloon, wherein the shaft defines at least a portion of the inflation lumen and a rider lumen, and wherein the inflation lumen is longer than the rider lumen and wherein a proximal portion of the inflation lumen wraps around the inner guide member in a helical shape, and
      a balloon advancement member disposed in a slot formed in the handle, the balloon advancement member configured to advance the balloon catheter over the inner guide member;

advancing the inner guide member to a desired location in a drainage pathway of the sinus cavity;

advancing the balloon over the inner guide member with the balloon advancement member, wherein advancing the balloon places the balloon at the desired location; and inflating the balloon with an inflation device coupled to the inflation port.

2. The method of claim 1, further comprising tracking the movement of the inner guide member into a frontal recess using an image guided surgery system.

3. The method of claim 2, wherein the image guided surgery system comprises a CT guidance system.

4. The method of claim 1, wherein the inner guide member includes a lumen and, prior to inflating the balloon, a guide wire is inserted into the lumen and advanced until a distal portion of the guide wire extends from a distal end of the inner guide member.

5. The method of claim 1, wherein the handle is fixed to the inner guide member.

6. The method of claim 1, further including adjusting a shape of the inner guide member prior to advancing the inner guide member to the desired location.

7. The method of claim 6, wherein the shape is adjusted by replacing the inner guide member with a second inner guide member.

8. The method of claim 6, wherein the shape is adjusted by manually bending the inner guide member.

9. The method of claim 1, wherein the inner guide member defines a lumen and the method further includes coupling the lumen to an aspiration source and aspirating the sinus cavity.

10. The method of claim 1, wherein the sinus cavity is a maxillary sinus cavity.

11. The method of claim 1, wherein the sinus cavity is a sphenoid sinus cavity.

12. The method of claim 1, wherein a user grasps the handle with a first hand and the lighted instrument with a second hand.

13. The method of claim 1, wherein the inner guide member includes a lumen and, prior to inflating the balloon, the lighted instrument is advanced distally inside the lumen and illuminates at least a portion of the sinus cavity.

* * * * *